United States Patent
Gavai et al.

(10) Patent No.: US 7,402,582 B2
(45) Date of Patent: *Jul. 22, 2008

(54) PYRROLOTRIAZINE COMPOUNDS USEFUL AS KINASE INHIBITORS AND METHODS OF TREATING KINASE-ASSOCIATED CONDITIONS THEREWITH

(75) Inventors: Ashvinikumar V. Gavai, Princeton Junction, NJ (US); Ping Chen, Belle Mead, NJ (US); Derek J. Norris, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/475,808

(22) Filed: Jun. 27, 2006

(65) Prior Publication Data

US 2007/0004732 A1 Jan. 4, 2007

Related U.S. Application Data

(60) Provisional application No. 60/771,389, filed on Feb. 8, 2006, provisional application No. 60/696,394, filed on Jul. 1, 2005.

(51) Int. Cl.
  *C07D 487/04* (2006.01)
  *C07D 403/12* (2006.01)
  *C07D 403/14* (2006.01)
  *A61K 31/4155* (2006.01)
  *A61K 31/4162* (2006.01)
  *A61K 31/53* (2006.01)
  *A61K 19/02* (2006.01)
  *A61K 35/00* (2006.01)

(52) U.S. Cl. ...................... 514/243; 544/183
(58) Field of Classification Search ................ 544/183; 514/243
See application file for complete search history.

(56) References Cited

U.S. PATENT DOCUMENTS

| | | |
|---|---|---|
| 6,670,357 B2 | 12/2003 | Leftheris et al. |
| 6,869,952 B2 | 3/2005 | Perry |
| 6,916,815 B2 | 7/2005 | Vite et al. |
| 6,951,859 B2 | 10/2005 | Bhide et al. |
| 6,969,717 B2 | 11/2005 | Bhide et al. |
| 6,982,265 B1 | 1/2006 | Hunt et al. |
| 7,102,002 B2 | 9/2006 | Cai et al. |
| 2004/0082582 A1 | 4/2004 | Dyckman et al. |
| 2006/0004006 A1 | 1/2006 | Borzilleri et al. |

FOREIGN PATENT DOCUMENTS

| | | |
|---|---|---|
| WO | WO00/71129 | 11/2000 |
| WO | WO02/40486 | 5/2002 |
| WO | WO2004/009784 | 1/2004 |
| WO | WO2004/013145 | 2/2004 |

OTHER PUBLICATIONS

Cecil Textbook of Medicine, edited by Bennet, J.C., and Plum F., 20th edition, vol. 1, 1004-1010, 1996.*
Mass, R. D., Int. J. Radiation Oncology Bio. Phys.vol. 58(3): 932-940, 2004.*
Fabbro et al. Pharmacology & therapeutics 93, 79-98, 2002.*
U.S. Appl. No. 60/740,704, filed Nov. 30, 2005, Bristol-Myers Squibb Company.
U.S. Appl. No. 11/475,816, filed Jun. 27, 2006, Bristol-Myers Squibb Company.

* cited by examiner

*Primary Examiner*—Venkataraman Balasubramanian
(74) *Attorney, Agent, or Firm*—Fitzpatrick, Cella, Harper & Scinto

(57) ABSTRACT

The invention relates to at least one pyrrolotriazine derivative, at least one pharmaceutical composition comprising at least one pyrrolotriazine derivative, and at least one method of using at least one pyrrolotriazine derivative to treat at least one kinase associated condition.

23 Claims, No Drawings

PYRROLOTRIAZINE COMPOUNDS USEFUL AS KINASE INHIBITORS AND METHODS OF TREATING KINASE-ASSOCIATED CONDITIONS THEREWITH

CROSS-REFERENCE TO RELATED APPLICATIONS

This application claims the benefit of U.S. Provisional Application No. 60/696,394, filed Jul. 1, 2005 and U.S. Provisional Application No. 60/771,389, filed Feb. 8, 2006, the contents of which are both hereby incorporated herein by reference.

FIELD OF THE INVENTION

Disclosed herein is at least one pyrrolotriazine derivative, at least one pharmaceutical composition comprising at least one pyrrolotriazine derivative described herein, and at least one method of using at least one pyrrolotriazine derivative disclosed herein for treating at least one kinase associated condition.

BACKGROUND OF THE INVENTION

Hyperproliferative diseases, such as, for example, cancer are generally characterized by uncontrolled cellular proliferation and/or disruption in programmed cell death. The loss of a cell's ability to control cellular proliferation is often caused by genetic damage to the cellular pathways responsible for regulating cellular functions, including but not limited to, for example, metabolism, cell cycle progression, cell adhesion, vascular function, apoptosis, and angiogenesis. As a result, one approach to treating hyperproliferative diseases has involved targeting at least one protein involved in regulating these cellular functions.

The protein kinases are at least one class of proteins that has been identified as playing an important role in regulating cellular functions. Indeed, many diseases are associated with abnormal cellular responses triggered by protein kinase-mediated events. Such diseases include but are not limited to autoimmune diseases, bone diseases, inflammatory diseases, metabolic diseases, neurological and neurodegenerative diseases, cancer, cardiovascular diseases, allergies and asthma, Alzheimer's disease, and hormone related diseases.

The protein kinases are a large and diverse group of enzymes that are divided into groups based on the particular amino acids (serine/threonine, tyrosine, lysine and histidine) that a particular kinase targets. For example, receptor and non-receptor tyrosine kinases target tyrosine kinase and cyclin dependent kinases (CDKs) and mitogen activated protein kinases (MAPKs) target both tyrosine and serine/threonine.

Exemplary protein kinases, include, but are not limited to, for example, receptor tyrosine kinases (RTKs), such as, for example, growth factors including, for example, type III receptor tryrosine kinase (Flt3); non-receptor tyrosine kinases, such as, for example, Src kinases including, for example, Src, Yes, Fyn, Lyn, Lck, Blk, Hck, Fgr, and Yrk, Btk kinases, Csk kinases, ZAP70 kinases, and Kak kinases; serine/threonine kinases, such as, for example, p90 ribosomal S6 kinases (RSK), including, for example, RSK1/p90Rsk, RSK2, RSK3, and RSK4, checkpoint protein kinases, including, for example, CHK1 and CHK2, AURORA kinases, including, for example, aurora-A, aurora-B, and aurora-C, and Glycogen synthase kinase 3 (GSK3); cyclin dependent kinases (CDKs) including, for example, CDK1, CDK2, CDK4, CDK5, CDK6, CDK 7, and cell division control 2 protein (CDC2); and mitogen-activated protein kinases (MAPKs), such as, for example, mitogen-activated protein kinase 1 (ERK), MAPK3, MAPK7, mitogen-activated protein kinase 8 (JNK1), mitogen-activated protein kinase 14 (p38 alpha), MAPK 10, JNK 3 alpha protein kinase, stress-activated protein kinase JNK 2, and MAPK 14.

More recently, the Aurora kinases were discovered to be involved in the growth of various types of cancer cells, and as a result are being targeted to develop potential cancer treatments. Accordingly, efforts have been undertaken to develop Aurora kinase inhibitors that are therapeutically effective against cancer cells.

SUMMARY OF THE INVENTION

Described herein are compounds of Formula (I):

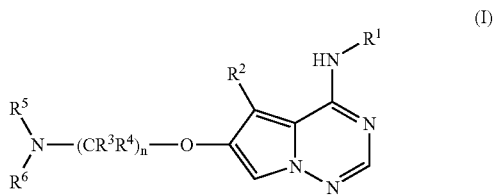

or a pharmaceutically acceptable salt thereof, wherein:
$R^1$ is

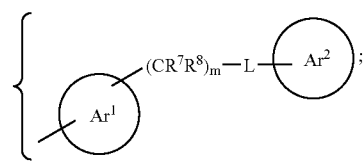

$R^2$ is H, lower alkyl, halogen, or $-OR^9$;
$R^3$ and $R^4$ are independently selected from H, lower alkyl, substituted lower alkyl, $-OR^{10}$, and $NR^{11}R^{12}$;
n is 2, 3, 4, 5, or 6;
$R^5$ and $R^6$ are independently selected from H, alkyl, and substituted alkyl, or taken together with the nitrogen to which they are attached form a 4-, 5-, 6-, or 7-membered heterocyclic or substituted heterocyclic ring optionally containing at least two heteroatoms;
$R^7$ and $R^8$ are independently selected from H, alkyl, and substituted alkyl;
m is 1, 2, or 3;
L is $-OC(=O)NH-$, $-O-$, $-C(=O)NH-$, $-NHC(=O)-$, or $-NHS(=O)_2-$;
$R^9$ is H, or lower alkyl;
$R^{10}$ is H, alkyl, substituted alkyl, alkylamino, or substituted alkylamino;
$R^{11}$ and $R^{12}$ are independently selected from H, alkyl, and substituted alkyl; and Ar¹ and Ar² are independently selected from aryl, substituted aryl, heteroaryl, and substituted heteroaryl.

Further described herein is at least one pharmaceutical composition comprising a therapeutically effective amount of at least one compound of Formula (I); optionally at least one pharmaceutically-acceptable carrier and/or diluent; and optionally at least one other anti-cancer agent.

Even further described herein is at least one method for treating at least one proliferative disease comprising administering to a patient in need thereof a therapeutically effective amount of at least one compound of Formula (I); optionally administering either simultaneously or sequentially at least one other anti-cancer agent; and optionally administering either simultaneously or sequentially at least one other anti-cancer treatment.

Yet even further described herein is at least one Formula (I) compound selected from (i) 2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-(3-methylphenyl)acetamide; N-(3-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-chloro-4-fluorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(4-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[4-(hydroxymethyl)piperidin-1-yl]propyl}oxy)pyrrolo[2,1-f][1,2,4]triazin-4-yl]amino}-1,3-thiazol-5-yl)acetamide; 2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-phenylacetamide; N-(3-fluorophenyl)-2-(2-{[6-({3-[(2S)-2-(hydroxymethyl)pyrrolidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[(2S)-2-(hydroxymethyl)pyrrolidin-1-yl]propyl}oxy)pyrrolo[2,1-f][1,2,4]triazin-4-yl]amino}-1,3-thiazol-5-yl)acetamide; N-(3-fluorophenyl)-2-(2-(5-methyl-6-(3-(4-methyl-1-piperazinyl)propoxy)pyrrolo[2,1-f][1,2,4]triazin-4-yl)amino)-1,3-thiazol-5-yl)acetamide; N-(3-fluorophenyl)-2-(2-((6-(3-(4-(2-hydroxyethyl)-1-piperazinyl)propoxy)-5-methylpyrrolo[2,1-f][1,2,4]triazin-4-yl)amino)-1,3-thiazol-5-yl)acetamide; N-(3-fluorophenyl)-2-[2-({5-methyl-6-[(3-morpholin-4-ylpropyl)oxy]pyrrolo[2,1-j][1,2,4]triazin-4-yl}amino)-1,3-thiazol-5-yl]acetamide; N-(3-fluorophenyl)-2-[2-({5-methyl-6-[(3-pyrrolidin-1-ylpropyl)oxy]pyrrolo[2,1-f][1,2,4]triazin-4-yl}amino)-1,3-thiazol-5-yl]acetamide; N-(3-fluorophenyl)-2-[2-({5-methyl-6-[(3-piperidin-1-ylpropyl)oxy]pyrrolo[2,1-f][1,2,4]triazin-4-yl}amino)-1,3-thiazol-5-yl]acetamide; 2-(2-{[6-({3-[ethyl(2-hydroxyethyl)amino]propyl}oxy)-5-methylpyrrolo[2,1-f][1,2,4]triazin-4-yl]amino}-1,3-thiazol-5-yl)-N-(3-fluorophenyl)acetamide; N-(3-fluorophenyl)-2-(2-{[6-({2-[4-(hydroxymethyl)piperidin-1-yl]ethyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[4-(hydroxymethyl)piperidin-1-yl]propyl}oxy)-5-(methyloxy)pyrrolo[2,1-f][1,2,4]triazin-4-yl]amino}-1,3-thiazol-5-yl)acetamide; N-(3-fluorophenyl)-2-(2-{[6-({3-[(2S)-2-(hydroxymethyl)pyrrolidin-1-yl]propyl}oxy)-5-(methyloxy)pyrrolo[2,1-f][1,2,4]triazin-4-yl]amino}-1,3-thiazol-5-yl)acetamide; 2-(2-{[6-({3-[(2S)-2-(hydroxymethyl)pyrrolidin-1-yl]propyl}oxy)-5-methylpyrrolo[2,1-j][1,2,4]triazin-4-yl]amino}-1,3-thiazol-5-yl)-N-phenylacetamide; N-(2-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; and methyl 2-(5-(6-(3-chloropropoxy)-5-methylpyrrolo[1,2-f][1,2,4]triazin-4-ylamino)-1H-pyrazol-3-yl)acetate; and (ii) pharmaceutically acceptable salts thereof.

DETAILED DESCRIPTION OF THE INVENTION

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Embodiments identified herein as exemplary or preferred are intended to be illustrative and not limiting.

Unless specifically stated otherwise herein, references made in the singular may also include the plural. For example, "a" and "an" may refer to either one, or one or more.

The definitions set forth herein take precedence over definitions set forth in any patent, patent application, and/or patent application publication incorporated herein by reference.

Definitions of terms used in describing the invention are set forth hereinbelow. Unless otherwise indicated, the initial definition provided for a group or term applies each time such group or term is used individually or as part of another group.

Throughout the specification, groups and substituents thereof may be chosen by one skilled in the field to provide stable moieties and compounds.

Unless otherwise indicated, any heteroatom with unsatisfied valences is assumed to have hydrogen atoms sufficient to satisfy the valences.

The terms "alkyl" and "alk" refer to a straight chain or branched chain saturated hydrocarbon radical containing from 1 to 12 carbon atoms, preferably from 1 to 6 carbon atoms. Exemplary "alkyl" and/or "alk" groups include, but are not limited to, for example, methyl, ethyl, propyl, isopropyl, 1-methylpropyl, n-butyl, t-butyl, isobutyl, pentyl, hexyl, isohexyl, heptyl, 4,4-dimethylpentyl, diethylpentyl, octyl, 2,2,4-trimethylpentyl, nonyl, decyl, undecyl, and dodecyl.

The term "substituted alkyl" refers to an alkyl group substituted at any available and substitutable position with at least one substituent. Exemplary substituents include, but are not limited to, for example, hydrogen, alkyl, hydroxy (—OH), alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkenyl, substituted cycloalkenyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, —NR$^{aa}$(C=O)R$^{bb}$, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, substituted heteroalkyl, heteroalkenyl, substituted heteroalkenyl, heteroalkynyl, substituted heteroalkynyl, arylamino, arylalkylamino, alkanoylamino, arylamino, arylalkanoylamino, arylthio, arylalkylthio, arylsulfonyl, arylalkylsulfonyl, alkylsulfonyl, arylcarbonylamino, and alkylaminocarbonyl.

The term "lower alkyl" refers to an alkyl group containing from 1 to 4 carbon atoms. It is of import to note that although the term "lower alkyl" is encompassed within the definition of "alkyl", the usage of the term "lower alkyl" is not intended to limit the definition of the term "alkyl" either explicitly or implicitly to an optionally substituted straight- or branched-chain saturated hydrocarbon radical containing from 5 to 7 carbon atoms. Exemplary lower alkyl groups include, but are not limited to, for example, methyl; ethyl; propyl; isopropyl; n-butyl; t-butyl; isobutyl; pentyl; and isopentyl.

The term "substituted lower alkyl" refers to a lower alkyl substituted at any available and substitutable position with at least one alkyl, substituted alkyl, or substituent described above in defining the term "substituted alkyl" as an exemplary alkyl substituent.

The term "aryl" refers to monocyclic or bicyclic aromatic hydrocarbon rings having from 6 to 12 carbon atoms in the ring portion. Exemplary aryl groups include but are not limited to, for example, phenyl; naphthalenyl; biphenyl; and diphenyl groups. When two aromatic rings are present, the aromatic rings of the aryl group may either be joined at a single point (e.g., biphenyl), or be fused (e.g., naphthalenyl).

The term "substituted aryl" refers to an aryl substituted with at least one substituent at any available and substitutable ring position, or where valence allows on any rings fused or attached thereto. Exemplary substituents include, but are not limited to, for example, hydrogen; alkyl, substituted alkyl, hydroxy (—OH), alkoxy, alkoxyalkyl, alkoxycarbonyl, alkoxyarylthio, halogen, haloalkyl, haloalkoxy, aryloxy, arylalkyl, arylalkyloxy, alkanoyl, substituted alkanoyl, alkanoyloxy, alkanoylamino, amino, aminoalkyl, substituted aminoalkyl, alkylamino, substituted alkylamino, disubstituted amino, aminocarbonyl, arylamino, arylalkylamino, arylalkoxy, ureido, cyano, sulfonamide, substituted sulfonamide, heterocycloalkyl, substituted heterocycloalkyl, heterocycloalkylalkyl, cycloalkyl, substituted cycloalkyl, cycloalkylalkyl, cycloalkylalkyl, cycloalkylalkoxy, nitro, thio, thioalkyl, alkylthio, alkylsulfonyl, alkylsulfinyl, carboxy, carboxyalkyl, carboxyalkoxy, alkoxycarbonyl, alkylcarbonyloxy, carbamoyl, alkenyl, substituted alkenyl, alkynyl, substituted alkynyl, aryl, substituted aryl, arylsulfonylamino, arylalkenyl, aryloxycarbonyl, arylthio, arylthioalkyl, arylalkylthio, sulfonic acid, heteroaryl, substituted heteroaryl, heteroarylthio, heteroaryloxy, heteroarylalkenyl, heteroarylheteroaryl, heteroarylalkylthio, heteroaryloxyalkyl, alkylcarbonyl, aminocarbonylaryl, aminocarbonylalkyl, arylazo, alkoxycarbonylalkoxy, arylcarbonyl, alkylaminocarbonyl, aminoalkylcarbonyl, arylaminocarbonyl, alkylcarbonyloxy, arylcarbonyloxy, alkylcarbonylamino, arylcarbonylamino, arylsulfonyl, heteroarylsulfonyl, heterocycloalkylsulfonyl, arylsulfinyl, alkylsulfinyl, arylsulfinylalkyl, and arylsulfonylaminocarbonyl.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The terms "arylthioalkyl" or "arylsulfinylalkyl" refer to an arylthio or an arylsulfinyl, respectively, bonded to an alkyl or substituted alkyl.

The term "heteroaryl" refers to aromatic cyclic groups, such as, for example, 5- to 6-membered monocyclic, 7- to 11-membered bicyclic, or 10- to 16-membered tricyclic ring systems having at least one heteroatom in at least one carbon atom-containing ring. The carbon atom-containing ring may contain 1, 2, 3, or 4 heteroatom(s) selected from nitrogen, oxygen, and/or sulfur. The heteroaryl group may be attached to another moiety at any available point of attachment.

Exemplary monocyclic heteroaryl groups include, but are not limited to, for example, pyrazolyl, imidazolyl, triazolyl, oxazolyl, furyl, thiazolyl, isoxazolyl, thiazolyl, pyridyl [i.e.,

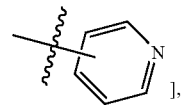
], pyridazinyl [i.e.,

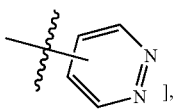

], pyrimidinyl [i.e.,

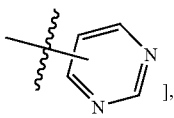

], pyrazinyl [i.e.,

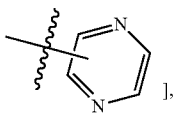

], and triazinyl. Unless reference is made to a specific point of attachment, e.g., as in pyrid-2-yl, pyridazin-3-yl, it is intended that such heteroaryl groups can be bonded to another moiety at any available point of attachment.

Exemplary bicyclic heteroaryl groups include, but are not limited to, for example, benzothiazolyl, benzoxazolyl, benzoxadiazolyl, benzothienyl, quinolinyl, chromenyl, indolyl, indazolyl, isoquinolinyl, benzimidazolyl, benzopyranyl, benzofuryl, benzofurazanyl, benzopyranyl, cinnolinyl, quinoxalinyl, pyrrolopyridyl, furopyridinyl (such as furo[2,3-c]pyridinyl, furo[3,2-b]pyridinyl] or furo[2,3-b]pyridinyl), and triazinylazepinyl.

The term "substituted heteroaryl" refers to a heteroaryl substituted at any available and substitutable ring position, or where valence allows on any rings fused or attached thereto, with at least one aryl, substituted aryl, or substituent described above in defining the term "substituted aryl" as an exemplary aryl substituent.

The terms "heteroaryloxy", "heteroarylalkenyl", "heteroarylheteroaryl", "heteroarylalkyl", "heteroarylalkoxy", "heteroarylthio", "heteroarylsulfonyl", or "heteroarylalkylthio" refer to a heteroaryl or substituted heteroaryl bonded to an oxygen; an alkenyl or substituted alkenyl; a heteroaryl or substituted heteroaryl; an alkyl or substituted alkyl; an alkoxy; a thio; a sulfonyl; or an alkylthio, respectively.

The term "heteroaryloxyalkyl" refers to a heteroaryloxy bonded to an alkyl or substituted alkyl.

The term "heterocyclic ring" refers to a stable, fully saturated or partially unsaturated 4-, 5-, 6- or 7-membered monocyclic ring system, which contains at least one heteroatom. In one embodiment, the at least one heteroatom is selected from nitrogen, sulfur and/or oxygen. In another embodiment, the heterocyclic ring is a 4-, 5-, 6- or 7-membered monocyclic ring containing one, two, or three heteroatoms selected from nitrogen, oxygen, and/or sulfur. In yet another embodiment, the heterocyclic ring is a 4-, 5-, 6- or 7-membered monocyclic ring containing one or two heteroatoms selected from nitrogen and oxygen. In a further embodiment, the heterocyclic ring is a 5-, or 6-membered monocyclic ring containing one, two, or three heteroatoms selected from nitrogen, oxygen, and/or sulfur. In an even further embodiment, the heterocyclic ring is a 5-, or 6-membered monocyclic ring containing one or two heteroatoms selected from nitrogen and oxygen.

Exemplary heterocyclic rings include, but are not limited to, for example, pyrrolidinyl, piperazinyl, piperidyl, morpholinyl, and homopiperazinyl.

The term "substituted heterocyclic ring" refers to a heterocyclic ring substituted at any available and substitutable ring position, or where valence allows on any rings fused or attached thereto, with at least one aryl, substituted aryl, or substituent described above in defining the term "substituted aryl" as an exemplary aryl substituent.

The term "cycloalkyl" refers to a fully saturated and partially unsaturated cyclic hydrocarbon group containing from 1 to 3 rings and 3 to 8 carbons per ring. Exemplary cycloalkyls include, but are not limited to, for example, cyclopropyl, cyclobutyl, cyclopentyl, cyclohexyl, cycloheptyl, cyclobutenyl, cyclopentenyl, and cyclohexenyl. A cycloalkyl ring may have a carbon ring atom replaced with a carbonyl group (C=O). Cycloalkyls include rings having a second or third ring fused thereto that is a heterocyclo, substituted heterocyclo, heteroaryl, substituted heteroaryl, aryl, or substituted aryl, provided that in such cases the point of attachment is to the cycloalkyl portion of the ring system. The term "cycloalkyl" also includes rings having a second or third ring attached to the ring or ring system in a spiro fashion.

The term "substituted cycloalkyl" refers to a cycloalkyl substituted with at least one substituent, preferably 1 to 4 substituents, more preferably 1 to 2 substituents, at any available point of attachment on either the cycloalkyl ring, or where valence allows on any rings fused or attached thereto. Exemplary substituents include, but are not limited to, for example, alkyl, substituted alkyl, and the substituents described in defining the term "substituted alkyl" as exemplary alkyl substituents.

Exemplary cycloalkyls include, but are not limited to, for example,

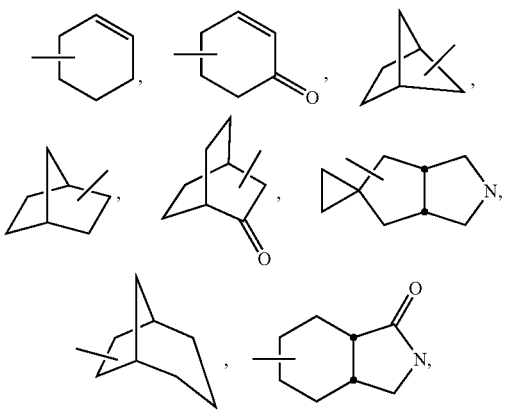

-continued

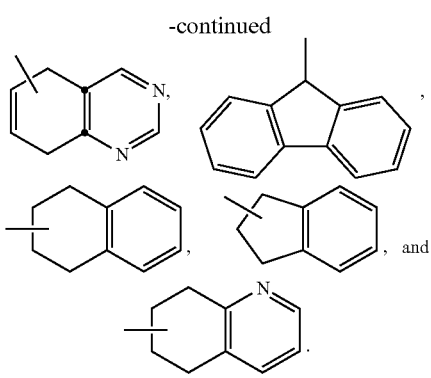

The term "heterocycloalkyl" refers to a saturated or unsaturated cycloalkyl in which one or more carbons (and any associated hydrogen atoms) are independently replaced with at least one heteroatom selected from O and N.

The term "substituted heterocycloalkyl" refers to a heterocycloalkyl substituted at any available and substitutable ring position with at least one alkyl, substituted alkyl, or substituent described above in defining the term "substituted alkyl" as an exemplary alkyl substituent.

The terms "heterocycloalkylalkyl" or "heterocycloalkylsulfonyl" refer to a heterocycloalkyl or substituted heterocycloalkyl bonded to an alkyl or substituted alkyl or a sulfonyl, respectively.

The terms "heterocycle" or "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocycle or heterocyclo containing a heteroatom may have 1, 2 or 3 heteroatoms selected from N, O, and S, where the N and S heteroatoms may optionally be oxidized and the N heteroatom may optionally be quaternized. The heterocycle or heterocyclo may be attached at any heteroatom or carbon atom.

Exemplary monocyclic heterocycle(s) or heterocyclo(s) include, but are not limited to, for example, pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl.

Exemplary bicyclic heterocycle(s) or heterocyclo(s) include, but are not limited to, for example, 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, and thienothienyl.

The terms "substituted heterocycle" or "substituted heterocyclo" refer to a heterocycle or heterocyclo, respectively, substituted at any available point of attachment, or where valence allows on any rings fused or attached thereto, with at least one alkyl, substituted alkyl, or substituent described above in defining the term "substituted alkyl" as an exemplary alkyl substituent.

The terms "heteroalkyl", "heteroalkenyl", and "heteroalkynyl" refer to a alkyl, alkenyl, and alkynyl, respectively, in which one or more of the carbon atoms (and any associated hydrogen atoms) are each independently replaced with the same or different heteroatom. Typical heteroatoms include, but are not limited to, for example, —O—, —S—, —O—O—, —S—S—, —O—S—, —NR$^a$—, =N—N=, —N=N—, —N=N—NR$^a$, —PH—, —P(O)$_2$—, —O—P(O)$_2$—, —S(O)—, —S(O)$_2$—, an —SnH$_2$—, wherein R$^a$ is hydrogen, alkyl, substituted alkyl, cycloalkyl, substituted cycloalkyl, aryl, or substituted aryl.

The terms "substituted heteroalkyl", "substituted heteroalkenyl", or "substituted heteroalkynyl" refer to a heteroalkyl, heteroalkenyl, or heteroalkynyl, respectively, substituted with at least one alkyl, substituted alkyl, or substituent described above in defining the term "substituted alkyl" as an exemplary alkyl substituent.

The term "hydroxyalkyl" refers to an —R$^b$OH, wherein R$^b$ is an alkyl or substituted alkyl.

The term "amino" refers to —NH$_2$.

The term "aminoalkyl" refers to an alkyl substituted with an amino having at least one hydrogen replaced with a group chosen from alkyl, alkenyl, and cycloalkyl. Thus, aminoalkyl refers to the group —R$^c$NR$^d$R$^e$, wherein R$^c$ is an alkyl and R$^d$ and R$^e$ are independently selected from hydrogen, alkyl, alkenyl, and cycloalkyl, provided R$^d$ and R$^e$ are not both hydrogen.

The term "substituted aminoalkyl" refers to an aminoalkyl wherein at least one of the alkyl, alkenyl, or cycloalkyl moieties is substituted with at least one, preferably 1 to 4, more preferably 1 to 2 groups selected from those recited herein as appropriate for the recited moiety. Thus, for example, a substituted aminoalkyl refers to the group —R$^c$NR$^d$R$^e$, wherein R$^c$ is an alkyl or substituted alkyl and R$^d$ and R$^e$ are independently selected from hydrogen, alkyl, substituted alkyl, alkenyl, substituted alkenyl, cycloalkyl, and substituted cycloalkyl, provided R$^d$ and R$^e$ are not both hydrogen, as in that case the group is amino and not substituted aminoalkyl.

The term "alkylamino" refers to an amino having at least one hydrogen replaced with a group chosen from alkyl, alkenyl, and cycloalkyl. Thus, alkylamino refers to the group —NR$^f$R$^g$, wherein R$^f$ and R$^g$ are independently selected form H, alkyl, alkenyl, and cycloalkyl, provided at least one of R$^f$ or R$^g$ is an alkyl.

The term "substituted alkylamino" refers to an alkylamino wherein at least one of the alkyl, alkenyl, or cycloalkyl moieties is substituted with at least one, preferably 1 to 4, more preferably 1 to 2 groups selected from those recited herein as appropriate for the recited moiety. Thus, for example, a substituted alkylamino refers to the group —NR$^f$R$^g$, wherein R$^f$ and R$^g$ are independently selected form H, alkyl, substituted alkyl, alkenyl, substituted alkenyl, cycloalkyl, and substituted cycloalkyl, provided at least one of R$^f$ or R$^g$ is an alkyl and at least one of R$^f$ or R$^g$ is a substituted moiety.

The term "disubstituted amino" refers to an amino having both hydrogens replaced with a group chosen from alkyl, substituted alkyl, alkenyl, substituted alkenyl, cycloalkyl, and substituted cycloalkyl. Thus, for example, a disubstituted amino refers to the group —NR$^h$R$^i$, wherein R$^h$ and R$^i$ are independently selected from alkyl, substituted alkyl, alkenyl, substituted alkenyl, cycloalkyl, and substituted cycloalkyl.

The terms "halogen" and "halo" refer to chlorine, bromine, fluorine, and iodine.

The terms "haloalkyl" or "haloalkoxy" refer to an alkyl or substituted alkyl; or an alkoxy, respectively, bonded to a single halogen or multiple halogens. Exemplary haloalkyls containing multiple halogens include, but are not limited to, for example, —CHCl$_2$ and —CF$_3$. Exemplary haloalkoxys containing multiple halogens include, but are not limited to, for example, trifluoromethoxy (—OCF$_3$).

The term "alkoxy" refers to an alkyl, substituted alkyl, alkanoyl, substituted alkanoyl, cycloalkyl or substituted cycloalkyl bonded through an oxygen linkage (—O-alkyl, —O-substituted alkyl, —O-alkanoyl, —O-substituted alkanoyl, —O-cycloalkyl, or —O-substituted cycloalkyl). Exemplary alkoxy groups include, but are not limited to, for example, methoxy, ethoxy, propoxy, isopropoxy, n-butoxy, t-butoxy, isobutoxy, pentoxy, isopentoxy, hexoxy, heptoxy, pentoxy, decanoxy, undecanoxy, and dodecanoxy.

The terms "alkoxyalkyl" or "alkoxyarylthio" refer to an alkyl or substituted alkyl; or an arylthio, respectively, bonded to an alkoxy.

The term "alkenyl" refers to a straight or branched chain hydrocarbon radical containing from 2 to 12 carbon atoms and at least one carbon-carbon double bond. Exemplary alkenyls include, but are not limited to, for example, ethenyl and allyl.

The term "substituted alkenyl" refers to an alkenyl substituted with at least one substituent, preferably 1 to 4 substituents, more preferably 1 to 2 substituents at any available point of attachment. Exemplary substituents include, but are not limited to, for example, alkyl, substituted alkyl, and the substituents described above in defining the term "substituted alkyl" as exemplary alkyl substituents.

The term "cycloalkenyl" refers to a cyclized alkenyl.

The term "substituted cycloalkenyl" refers to a cyclized substituted alkenyl.

The term "alkanoyl" refers to an alkyl bonded through a carbonyl (i.e. —C(=O)R$^j$, wherein R$^j$ is an alkyl).

The term "substituted alkanoyl' refers to an alkanoyl substituted with at least one substituent, preferably 1 to 4 substituents, more preferably 1 to 2 substituents, at any available point of attachment. Exemplary substituents include, but are not limited to, for example, alkyl, substituted alkyl, and the substituents described above in defining the term "substituted alkyl" as exemplary alkyl substituents.

The terms "alkanoylamino", "arylcarbonylamino", "alkylcarbonylamino", or "arylsulfonylamino" refer to an alkanoyl or substituted alkanoyl; an arylcarbonyl; an alkylcarbonyl; or an arylsulfonyl, respectively, bonded to an amino.

The term "alkanoyloxy" refers to an alkanoyl or substituted alkanoyl bonded to an oxygen.

The term "alkynyl" refers to a straight or branched chain hydrocarbon radical containing from 2 to 12 carbon atoms and at least one carbon-carbon triple bond. Exemplary alkynyls include, but are not limited to, for example, ethynyl; propynyls, such as, for example, prop-1-yn-1-yl and prop-2-yn-1-yl; and butynyls, such as, for example, but-1-yn-1-yl, but-1-yn-3-yl, and but-3-yn-1-yl.

The term "substituted alkynyl" refers to an alkynyl substituted with at least one substituent, preferably 1 to 4 substituents, more preferably 1 to 2 substituents at any available point of attachment. Exemplary substituents include, but are not limited to, for example, alkyl, substituted alkyl, and the substituents described above in defining the term "substituted alkyl" as exemplary alkyl substituents.

The term "alkylsulfone" refers to —R$^k$S(=O)$_2$R$^k$, wherein R$^k$ is an alkyl or substituted alkyl.

The term "oxo" refers to the divalent radical =O.

The term "carbamate" refers to the group —OC(=O)NH$_2$.

The term "amide" refers to the group —C(=O)NH$_2$.

The term "sulfonamide" refers to the group —SO$_2$NH$_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —C(=O)NR$^m$R$^n$ wherein R$^m$ and R$^n$ are independently selected from H, alkyl, substituted alkyl, alkenyl, substituted alkenyl, cycloalkyl, and substituted cycloalkyl, provided at least one of R$^m$ or R$^n$ is a substituted moiety.

A substituted sulfonamide, for example, refers to the group —SO$_2$NR$^o$R$^p$ wherein R$^o$ and R$^p$ are independently selected from alkyl, substituted alkyl, alkenyl, substituted alkenyl, cycloalkyl, and substituted cycloalkyl, provided at least one of R$^o$ or R$^p$ is a substituted moiety.

A substituted carbamate, for example, refers to the group —OC(=O)NR$^q$R$^r$ wherein R$^q$ and R$^r$ are independently selected from alkyl, substituted alkyl, alkenyl, substituted alkenyl, cycloalkyl, and substituted cycloalkyl, provided at least one of R$^q$ or R$^r$ is a substituted moiety.

The term "ureido" refers to the group —NHC(=O)NH$_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —N(O)$_2$.

The term "thio" refers to the group —SH.

The term "thioalkyl" refers to the group —SR$^s$, wherein R$^s$ is an alkyl, substituted alkyl, cycloalkyl, or substituted cycloalkyl.

The term "alkylthio" refers to the group —R$^t$S where R$^t$ is an alkyl, substituted alkyl, cycloalkyl, or substituted cycloalkyl.

The term "alkylsulfonyl" refers to the group —S(=O)$_2$R$^u$ where R$^u$ is an alkyl, substituted alkyl, cycloalkyl, or substituted cycloalkyl.

The term "alkylsulfinyl" refers to the group —S(=O)R$^v$ where R$^v$ is an alkyl, substituted alkyl, cycloalkyl, or substituted cycloalkyl.

The term "carboxy" refers to the group —C(=O)OH.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —C(=O)OR$^w$ where R$^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —OC(=O)R$^x$, where R$^x$ is an alkyl or substituted alkyl, or an aryl or substituted aryl, respectively.

The term "carbamoyl" refers to the groups —OC(=O)NH$_2$, —OC(=O)NHR$^y$, and/or —OC(=O)NR$^y$R$^z$, wherein R$^y$ and R$^z$ are independently selected from alkyl and substituted alkyl.

The group —NR$^{aa}$(C=O)R$^{bb}$ refers to a group where R$^{aa}$ is selected from hydrogen and lower alkyl, and R$^{bb}$ is selected from hydrogen, alkyl, substituted alkyl, alkoxy, aminoalkyl, substituted aminoalkyl, alkylamino, substituted alkylamino, aryl, and substituted aryl.

The term "carbonyl" refers to a —C(=O).

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group S(=O)$_2$.

The term "sulfinyl" refers to an S(=O).

The term "carboxyalkyl" refers to an alkyl or substituted alkyl bonded to a carboxy.

As used herein, the term "patient" encompasses all mammalian species. A mammalian species includes, but is not limited to, for example, humans and domestic animals, such as, for example, dogs, cats, and horses.

The term "salt(s)", as employed herein, denotes acidic and/or basic salts formed with inorganic and/or organic acids and/or bases, and such term, as used herein, further includes zwitterion(s) ("inner salts").

The terms "zwitterion(s)", as employed herein, denote compound(s) containing both a basic moiety, including but not limited to, for example, pyridine and imidazole; and an acidic moiety including but not limited to, for example, a carboxylic acid.

The term "pharmaceutically acceptable", as employed herein, indicates the subject matter being identified as "pharmaceutically acceptable" is suitable and physiologically acceptable for administration to a patient. For example, the term "pharmaceutically acceptable salt(s)" denotes suitable and physiologically acceptable salt(s) for administration to a patient.

The compounds of Formula (I) can also form salt(s). As a result, when a compound of Formula (I) is referred to herein, such reference includes, unless otherwise indicated, salts thereof. In one embodiment, the compounds of Formula (I) form pharmaceutically acceptable salts. In another embodiment, the compounds of Formula (I) form salts that can, for example, be used to isolate and/or purify the compounds of Formula (I). Salt(s) of the Formula (I) compounds can be formed by, for example, reacting a Formula (I) compound with, for example, an equivalent amount of acid or base in a medium that allows the thusly formed salt to, for example, either precipitate out, or be isolated via lyophilization.

Exemplary acidic salt(s) the compounds of Formula (I) can form with inorganic and/or organic acids include, but are not limited to, for example, acetates, such as are formed with acetic or trihaloacetic acid; adipates; alginates; ascorbates; aspartates; benzoates; benzenesulfonates; bisulfates; borates; butyrates; citrates; camphorates; camphorsulfonates; cyclopentanepropionates; digluconates; dodecylsulfates; ethanesulfonates; fumarates; glucoheptanoates; glycerophosphates; hemisulfates; heptanoates; hexanoates; hydrochlorides; hydrobromides; hydroiodides; hydroxyethanesulfonates, such as, for example, 2-hydroxyethanesulfonates; lactates; maleates; methanesulfonates; naphthalenesulfonates, such as, for example, 2-naphthalenesulfonates; nicotinates; nitrates; oxalates; pectinates; persulfates; phenylpropionates, such as, for example, 3-phenylpropionates; phosphates; picrates; pivalates; propionates; salicylates; succinates; sulfates, such as, for example, are formed with sulfuric acid; sulfonates; tartrates; thiocyanates; and toluenesulfonates, such as, for example, tosylates and undecanoates. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), and aralkyl halides (e.g. benzyl and phenethyl bromides) to quaternize basic nitrogen-containing groups. Such salts can be formed in accordance with methods known to a person of ordinary skill in the art.

All stereoisomer(s) and geometric isomer(s) of the compounds of Formula (I), either in admixture or in pure or substantially pure form are also contemplated herein. Specifically, all enantiomers, tautomers, and diastereomers of the compounds of Formula (I), as well as mixtures, compounds, racemic compounds, racemic mixtures, and racemates produced therefrom are contemplated herein. Even more particularly, all optically active isomers of the compounds of Formula (I), including pure or substantially pure optically active isomers, i.e., optically active isomers substantially free of other isomers.

When a compound containing a single enantiomer of a compound of Formula (I) is desired, such compound can be obtained by either resolution of the final product or by stereospecific synthesis from either isomerically pure starting material(s), or any convenient intermediate(s). Resolution of the final product, an intermediate, or a starting material can be effected by any suitable method known in the art, including, for example, physical methods, such as, for example, fractional crystallization, separation or crystallization of diastereomeric derivatives, and separation by chiral column chromatography. Individual optical isomers can be obtained from racemates through, for example, conventional methods, such as, for example, salt formation with an optically active acid followed by crystallization. The chiral centers of the compounds described herein can have the S or R configuration as defined by the IUPAC 1974 Recommendations.

Prodrug(s) and/or solvate(s) of the compounds of Formula (I) are further contemplated herein.

The term "prodrug(s)", as employed herein, denotes a compound that, upon administration to a subject, undergoes chemical conversion via metabolic and/or chemical processes in vivo to yield a compound and/or derivative of Formula (I), or a salt and/or solvate thereof. Various forms of prodrug(s) are well known in the art. For examples of such prodrug derivatives, see:

a) *Design of Prodrugs*, edited by H. Bundgaard, (Elsevier, 1985) and *Methods in Enzymology*, Vol. 112, p. 309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992).

The term "solvate", as employed herein, denotes a compound produced by the chemical interaction of at least one solvent with at least one solute comprising at least one compound of Formula (I). Exemplary solvates include, but are not limited to, for example, hydrates.

All numbers expressing quantities of ingredients, properties such as molecular weight, reaction conditions, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained by the invention. At the very least, and not as an attempt to limit the application of the doctrine of equivalents to the scope of the claims, each numerical parameter should at least be construed in light of the number of reported significant digits and by applying ordinary rounding techniques.

It is to be understood that each of the variously stated ranges is intended to be continuous so as to include each numerical parameter between the stated minimum and maximum value of each range. It is to be further understood that, while not intending to limit the applicability of the doctrine of equivalents to the scope of the claims, each numerical parameter should at least be construed in a manner consistent with the reported number of significant digits for each numerical parameter and by applying ordinary rounding techniques. It is to be even further understood that, while not intending to limit the applicability of the doctrine of equivalents to the scope of the claims, even though a number may be contained within a numerical range wherein at least one of the minimum and maximum numbers of the range is or is not preceded by the word "about", each numerical value contained within the range may or may not be preceded by the word "about". For Example, a range of about 1 to about 10 includes about 1, about 2, 2, about 3, 3, about 4, 4, about 5, 5, about 6, 6, about 7, 7, about 8, 8, about 9, 9, and about 10; a range of about 1.1 to about 3.2 includes about 1.1, about 1.2, 1.2, about 1.3, 1.3, about 1.4, 1.4, about 1.5, 1.5, about 1.6, 1.6, about 1.7, 1.7, about 1.8, 1.8, about 1.9, 1.9, about 2.0, 2.0, about 2.1, 2.1, about 2.2, 2.2, about 2.3, 2.3, about 2.4, 2.4, about 2.5, 2.5, about 2.6, 2.6, about 2.7, 2.7, about 2.8, 2.8, about 2.9, 2.9, about 3.0, 3.0, about 3.1, 3.1, and about 3.2; and a range of about 1 to 4 includes about 1, 2, about 2, 3, about 3, and 4.

Further, when an amount, concentration, or other value or parameter is given as a list of upper values and lower values, such listings are intended to include all ranges formed by pairing any upper value with any lower value, regardless of whether ranges are separately disclosed.

Described herein are compounds of Formula (I):

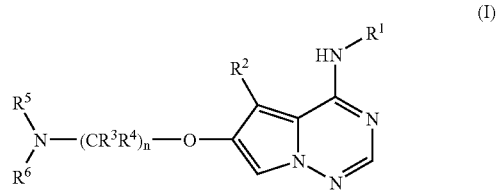

or a pharmaceutically acceptable salt thereof, wherein:
$R^1$ is

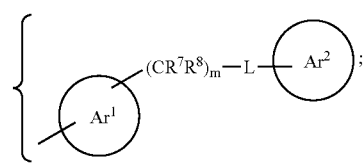

$R^2$ is H, lower alkyl, halogen, or $-OR^9$;

$R^3$ and $R^4$ are independently selected from H, lower alkyl, substituted lower alkyl, $-OR^{10}$, and $NR^{11}R^{12}$;

n is 2, 3, 4, 5, or 6;

$R^5$ and $R^6$ are independently selected from H, alkyl, and substituted alkyl, or taken together with the nitrogen to which they are attached form a 4-, 5-, 6-, or 7-membered heterocyclic or substituted heterocyclic ring optionally containing at least two heteroatoms;

R⁷ and R⁸ are independently selected from H, alkyl, and substituted alkyl;

m is 1, 2, or 3;

L is —OC(=O)NH—, —O—, —C(=O)NH—, —NHC(=O)—, or —NHS(=O)₂—;

R⁹ is H, or lower alkyl;

R¹⁰ is H, alkyl, substituted alkyl, alkylamino, or substituted alkylamino;

R¹¹ and R¹² are independently selected from H, alkyl, and substituted alkyl; and Ar¹ and Ar² are independently selected from aryl, substituted aryl, heteroaryl, and substituted heteroaryl.

In one embodiment, R¹ is selected from

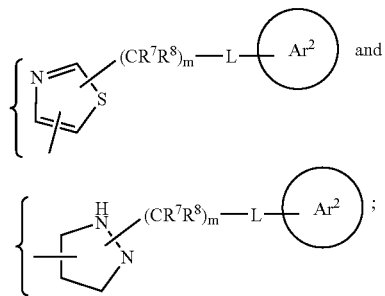

wherein R⁷, R⁸, m, Ar², and L are as defined hereinabove.

In another embodiment, R¹ is

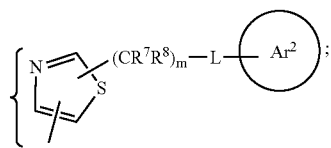

wherein R⁷, R⁸, m, Ar², and L are as defined hereinabove.

In yet another embodiment, R¹ is

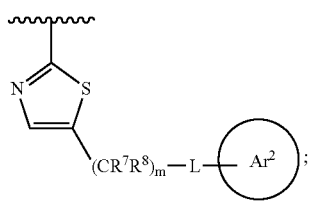

wherein R⁷, R⁸, m, Ar², and L are as defined hereinabove.

In a further embodiment, R¹ is selected from

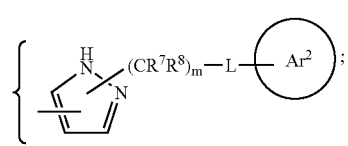

wherein R⁷, R⁸, m, Ar², and L are as defined hereinabove.

In yet a further embodiment, R¹ is

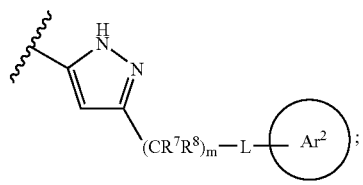

wherein R⁷, R⁸, m, Ar², and L are as defined hereinabove.

In yet another embodiment, R⁵ and R⁶ are taken together with the N to which they are attached to form a 4-, 5-, 6-, or 7-membered heterocyclic or substituted heterocyclic ring containing at least two heteroatoms selected from O, S, and N.

In yet a further embodiment, R⁵ and R⁶ are taken together with the N to which they are attached to form a 4-, 5-, 6-, or 7-membered heterocyclic or substituted heterocyclic ring containing at least two heteroatoms selected from O and N.

In even another embodiment, R⁵ and R⁶ are taken together with the N to which they are attached to form a 5- or 6-membered heterocyclic or substituted heterocyclic ring containing at least two heteroatoms selected from O, S, and N.

In even a further embodiment, R⁵ and R⁶ are taken together with the N to which they are attached to form a 5- or 6-membered heterocyclic or substituted heterocyclic ring containing at least two heteroatoms selected from O and N.

In still even a further embodiment, R⁵ and R⁶ are taken together with the N to which they are attached to form a morpholinyl.

In yet even another embodiment, R⁵ and R⁶ are taken together with the N to which they are attached to form a 5- or 6-membered substituted heterocyclic ring substituted with at least one substituent selected from alkyl and hydroxyalkyl.

In yet even a further embodiment, R⁵ and R⁶ are taken together with the N to which they are attached to form a 5- or 6-membered substituted heterocyclic ring containing at least two heteroatoms selected from O, S, and N, wherein the heterocyclic ring is substituted with at least one substituent selected from alkyl and hydroxyalkyl.

In still even a further embodiment, R⁵ and R⁶ are taken together with the N to which they are attached to form a 5- or 6-membered substituted heterocyclic ring containing at least two heteroatoms selected from O and N, wherein the heterocyclic ring is substituted with at least one substituent selected from alkyl and hydroxyalkyl.

In yet still a further embodiment, R⁵ and R⁶ are taken together with the N to which they are attached to form a 5- or 6-membered heterocyclic or substituted heterocyclic ring.

In still another embodiment, R² is hydrogen or lower alkyl.

In still yet another embodiment, R² is methyl, ethyl, or isopropyl.

In yet even a further embodiment, R³, R⁴, R⁷, and R⁸ are independently selected from hydrogen and lower alkyl.

In even a further embodiment, R³, R⁴, R⁷, and R⁸ are each hydrogen.

In yet another embodiment, L is —C(=O)NH— or —NHC(=O)—.

In a further embodiment, L is —C(=O)NH—.

In still a further embodiment, $Ar^2$ is aryl or substituted aryl.

In yet a further embodiment, $Ar^2$ is a substituted aryl substituted with at least one substituent selected from hydrogen, halogen, cyano, lower alkyl, and $OR^{13}$, wherein $R^{13}$ is a lower alkyl.

In still yet a further embodiment, $Ar^2$ is a substituted aryl substituted with at least one substituent selected from hydrogen and halogen.

In even yet another embodiment, $Ar^2$ is

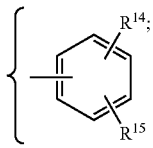

wherein $R^{14}$ and $R^{15}$ are independently selected from hydrogen, halogen, and methyl.

In an even further embodiment, $Ar^2$ is

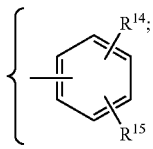

wherein $R^{14}$ and $R^{15}$ are independently selected from hydrogen and halogen.

In a still even further embodiment, n is 2 or 3.

In yet an even further embodiment, n is 3.

In still yet another embodiment, m is 1.

In another embodiment, $Ar^2$ is

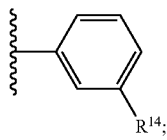

wherein R14 is hydrogen or halogen.

In a further embodiment, $Ar^2$ is

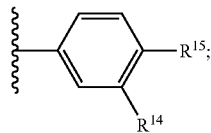

wherein $R^{14}$ and $R^{15}$ are independently selected from hydrogen and halogen.

Further described herein is at least one pharmaceutical composition comprising at least one compound in accordance with Formula (I), optionally at least one pharmaceutically-acceptable carrier and/or diluent, and optionally at least one other anti-cancer agent.

Even further described herein is a method for treating at least one proliferative disease comprising administering to a patient in need thereof an effective amount of at least one compound according to Formula (I), optionally administering either simultaneously or sequentially at least one other anti-cancer agent, and optionally administering either simultaneously or sequentially at least one other anti-cancer treatment.

The phrase "anti-cancer treatment" includes, but is not limited to, for example, radiation therapy and surgery.

The phrase "other anti-cancer agent" includes any known agent useful for treating cancer. Examples of other such anti-cancer agent(s) include, but are not limited to, for example, antiangiogenic agents, such as, for example, linomide, inhibitors of integrin αvβ3 function, angiostatin, and razoxane; antiestrogens, such as, for example, tamoxifen, toremifene, raloxifene, droloxifene, and iodoxifene; progestogens, such as, for example, megestrol acetate, hydroxyprogesterone, and medroxyprogesterone; aromatase inhibitors, such as, for example, anastrozole, testolactone, letrozole, borazole, and exemestane; antihormones, such as, for example, aminoglutethimide; synthetic estrogens, such as, for example, chlorotrianisene, diethylstilbestrol and 17 α-ethinylestradiol; synthetic androgens, such as for example, dromostanolone propionate, fluoxymesterone, and methyltestosterone; antiprogestogens; antiandrogens, such as, for example, flutamide, nilutamide, bicalutamide, and cyproterone acetate; androgens, such as, for example, testosterone; synthetic glucocorticoids, such as, for example, methylprednisolone, triamcinolone, prednisolone, and prednisone; LHRH agonists and antagonists, such as, for example, gosereline acetate and leuprolide; inhibitors of testosterone 5α-dihydroreductase, such as, for example, finasteride; farnesyltransferase inhibitors; anti-invasion agents, such as, for example, metalloproteinase inhibitors like marimastat and inhibitors of urokinase plasminogen activator receptor function; VEGF inhibitors, such as, for example, anti-VEGF antibodies (Avastin) and small molecules, such as, for example, ZD6474, SU6668, Vatalanib, BAY-43-9006, SU11248, CP-547632, and CEP-7055; Her 1 and Her 2 inhibitors including, for example, anti-Her 2 antibodies (Herceptin); EGFR inhibitors, such as, for example, gefitinib, erlotinib, ABX-EGF, EMD72000, 11F8, and cetuximab; Eg5 inhibitors, such as, for example, SB-715992, SB-743921, and MKI-833; pan Her inhibitors, such as, for example, canertinib, EKB-569, CI-1033, AEE-788, XL-647, mAb 2C4, and GW-572016; Src inhibitors, such as, for example, Gleevac and Dasatinib; MEK-1 inhibitors; MAPK inhibitors; PI3 kinase inhibitors; Met inhibitors; other Aurora kinase inhibitors; PDGF inhibitors, such as, for example, imatinib; IGF1R inhibitors, such as, for example, those disclosed in United States Patent Application No. 2004/0044203 A1; other receptor and non-receptor tyrosine kinase inhibitors; other serine/threonine kinase inhibitors; CDK inhibitors; antimetabolites, such as, for example, methotrexate, idatrexate, trimetrexate, 5-fluorouracil, tegafur, cytarabine, fludarabine, 6-thioguanine, DON (d-oxo-norleucine or AT-125) and 6-mercaptopurine; intercalating antitumor antibiotics, such as, for example, doxorubicin, daunomycin, epirubicin, idarubicin, mitomycin-C, dactinomycin, mitoxantrone, and mithramycin; platinum derivatives, such as, for example, cisplatin, oxaliplatin, and carboplatin; alkylating agents, such as, for example, nitrogen mustard, melphalan, chlorambucil, busulphan, cyclophosphamide, ifosfamide nitrosoureas, dacarbazine, hexamethyl melamine, estramustine, and thiotepa; antimitotic agents, such as, for example, vinblastine, vinflunine, Taxol® (paclitaxel), Taxotere® (docetaxel), 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, epothilone analogs, i.e., ixabepilone, and derivatives thereof; inhibitors of integrin signaling; topoisomerase inhibitors, such as, for example, etoposide, teniposide, amsacrine, doxorubicin, daunorubicin, irinotecan, and topotecan; cell cycle inhibitors, such as, for example, flavopyridols; biological response modifiers, such as, for example, interferon-alpha; monoclonal antibodies, such as for example, rituximab, and gemtuzumab ozogamicin; proteasome inhibitors, such as, for example, Velcade® (bortezomib); SN-8; procarbazine; L-asparaginase; pyridobenzoindole derivatives; ribonucleotide reductase inhibitors; mTOR inhibitors; leucovorin; VM-26; interleukins; and hematopoietic growth factors.

The proliferative disease that can be treated in accordance with the Formula (I) compounds of the invention include, but are not limited to, for example, Aurora kinase associated diseases, such as, for example, cancer, bone diseases, inflammatory diseases, autoimmune diseases, metabolic diseases, viral diseases, fungal diseases, neurological and neurodegenerative disorders, Alzheimer's disease, allergies and asthma, cardiovascular diseases, and hormone related diseases.

In one embodiment, at least one compound of Formula (I) is used to treat cancer.

The cancers Formula (I) compound(s) can be used to treat include, but are not limited to, for example, carcinoma, including, for example, that of the bladder, breast, colon, kidney, liver, lung (including small cell lung cancer), esophagus, gall bladder, ovary, pancreas, stomach, cervix, thyroid, prostate, and skin (including squamous cell carcinoma); hematopoietic tumors of lymphoid lineage, such as, for example, leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burkett's lymphoma; hematopoietic tumors of myeloid lineage, such as, for example, acute and chronic myelogenous leukemia, myelodysplastic syndrome, and promyelocytic leukemia; tumors of mesenchymal origin, including, for example, fibrosarcoma and rhabdomyosarcoma; tumors of the central and peripheral nervous system, including, for example, astrocytoma, neuroblastoma, glioma, and schwannomas; and other tumors, such as, for example, melanoma, seminoma, teratocarcinoma, osteosarcoma, xeroderma pigmentosum, keratoacanthoma, thyroid follicular cancer, and Kaposi's sarcoma.

Yet even further described herein are compounds according to Formula (I) including, but not limited to, for example, 2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-(3-methylphenyl)acetamide; N-(3-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-chloro-4-fluorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(4-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[4-(hydroxymethyl)piperidin-1-yl]propyl}oxy)pyrrolo[2,1-f][1,2,4]triazin-4-yl]amino}-1,3-thiazol-5-yl)acetamide; 2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-phenylacetamide; N-(3-fluorophenyl)-2-(2-{[6-({3-[(2S)-2-(hydroxymethyl)pyrrolidin-1-yl]propyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[(2S)-2-(hydroxymethyl)pyrrolidin-1-yl]propyl}oxy)pyrrolo[2,1-f][1,2,4]triazin-4-yl]amino}-1,3-thiazol-5-yl)acetamide; N-(3-fluorophenyl)-2-(2-((5-methyl-6-(3-(4-methyl-1-piperazinyl)propoxy)pyrrolo[2,1-f][1,2,4]triazin-4-yl)amino)-1,3-thiazol-5-yl)acetamide; N-(3-fluorophenyl)-2-(2-((6-(3-(4-(2-hydroxyethyl)-1-piperazinyl)propoxy)-5-methylpyrrolo[2,1-f][1,2,4]triazin-4-yl)amino)-1,3-thiazol-5-yl)acetamide; N-(3-fluorophenyl)-2-[2-({5-methyl-6-[(3-morpholin-4-ylpropyl)oxy]pyrrolo[2,1-f][1,2,4]triazin-4-yl}amino)-1,3-thiazol-5-yl]acetamide; N-(3-fluorophenyl)-2-[2-({5-methyl-6-[(3-pyrrolidin-1-ylpropyl)oxy]pyrrolo[2,1-f][1,2,4]triazin-4-yl}amino)-1,3-thiazol-5-yl]acetamide; N-(3-fluorophenyl)-2-[2-({5-methyl-6-[(3-piperidin-1-ylpropyl)oxy]pyrrolo[2,1-f][1,2,4]triazin-4-yl}amino)-1,3-thiazol-5-yl]acetamide; 2-(2-{[6-({3-[ethyl(2-hydroxyethyl)amino]propyl}oxy)-5-methylpyrrolo[2,1-f][1,2,4]triazin-4-yl]amino}-1,3-thiazol-5-yl)-N-(3-fluorophenyl)acetamide; N-(3-fluorophenyl)-2-(2-{[6-({2-[4-(hydroxymethyl)piperidin-1-yl]ethyl}oxy)-5-methylpyrrolo[2,1-f][1,2,4]triazin-4-yl]amino}-1,3-thiazol-5-yl)acetamide; N-(3-fluorophenyl)-2-(2-{[6-({3-[4-(hydroxymethyl)piperidin-1-yl]propyl}oxy)-5-(methyloxy)pyrrolo[2,1-f][1,2,4]triazin-4-yl]amino}-1,3-thiazol-5-yl)acetamide; N-(3-fluorophenyl)-2-(2-{[6-({3-[(2S)-2-(hydroxymethyl)pyrrolidin-1-yl]propyl}oxy)-5-(methyloxy)pyrrolo[2,1-f][1,2,4]triazin-4-yl]amino}-1,3-thiazol-5-yl)acetamide; 2-(2-{[6-({3-[(2S)-2-(hydroxymethyl)pyrrolidin-1-yl]propyl}oxy)-5-methylpyrrolo[2,1-f][1,2,4]triazin-4-yl]amino}-1,3-thiazol-5-yl)-N-phenylacetamide; N-(2-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide; methyl 2-(5-(6-(3-chloropropoxy)-5-methylpyrrolo[1,2-f][1,2,4]triazin-4-ylamino)-1H-pyrazol-3-yl)acetate; and pharmaceutically acceptable salts thereof.

Due to the key role protein kinases play in regulating cellular proliferation in general, inhibitors of such kinases may act as reversible cytostatic agents, thereby making such inhibitors useful to treat any disease process featuring abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula (I) may modulate apoptosis, and therefore may be useful in treating cancer, including but not limited to, for example, the cancers already mentioned herein above; treating viral infections, including but not limited to, for example, herpes virus, pox virus, Epstein-Barr virus, Sindbis virus, and adenovirus; preventing AIDS from developing in HIV-infected individuals; treating autoimmune diseases, including but not limited to, for example, systemic lupus, erythematosus, autoimmune mediated glomerulonephritis, rheumatoid arthritis, psoriasis, inflammatory bowel disease, and autoimmune diabetes mellitus; treating neurodegenerative disorders, including but not limited to, for example, Alzheimer's disease, AIDS-related dementia, Parkinson's disease, amyotrophic lateral sclerosis, retinitis pigmentosa, spinal muscular atrophy, and cerebellar degeneration; treating myelodysplastic syndromes; treating aplastic anemia; treating ischemic injury associated with myocardial infarctions, strokes, and reperfusion injury; treating arrhythmias; treating artherosclerosis; treating toxin-induced or alcohol related liver diseases; treating hematological diseases, including but not limited to, for example, chronic anemia and aplastic anemia; treating degenerative diseases of the musculoskeletal system, including but not limited to, for example, osteoporosis and arthritis; treating aspirin-sensitive rhinosinusitis; treating cystic fibrosis; treating multiple sclerosis; treating kidney diseases; and treating cancer pain.

Compounds of Formula (I) may also modulate the level of cellular RNA and DNA synthesis, and as a result could be useful in treating viral infections, including but not limited to, for example, HIV; human papilloma virus; herpes virus; pox virus; Epstein-Barr virus; Sindbis virus; and adenovirus.

Compounds of Formula (I) may also be useful in the chemoprevention of cancer. Chemoprevention is defined as inhibiting the development of invasive cancer by blocking the initiating mutagenic event, by blocking progression of pre-malignant cells that have already suffered an insult, or by inhibiting tumor relapse.

Compounds of Formula (I) may also be useful in inhibiting tumor angiogenesis and metastasis.

The compounds of Formula (I) may further be employed adjuvant to surgery. For example, at least one compound in accordance with Formula (I) may be used in combination with antibody therapy, or in concert with vaccine/immune modulating agents used to treat cancer.

In one embodiment, the patient is an animal.

In another embodiment, the patient is a human.

The compounds of Formula (I) can be administered by any means suitable for the condition to be treated, which can depend on the need for site-specific treatment or quantity of drug to be delivered.

A pharmaceutical composition comprising at least one compound according to Formula (I) can, for example, be delivered orally via any acceptable and suitable oral form, including but not limited to, for example, tablets; troches; lozenges; aqueous or oily suspensions; dispersible powders or granules; emulsions; hard or soft capsules; syrups; and elixirs. Pharmaceutical compositions intended for oral use can be prepared according to any method known in the art for manufacturing pharmaceutical compositions. In order to provide pharmaceutically elegant and palatable preparations, a pharmaceutical composition in accordance with the invention can contain at least one agent selected from sweetening agents, flavoring agents, coloring agents and preserving agents.

A tablet can be prepared by, for example, admixing at least one compound according to Formula (I) with at least one non-toxic pharmaceutically acceptable excipient suitable for the manufacture of tablets, including but not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. For example, water soluble taste masking materials, including but not limited to, for example, hydroxypropyl-methylcellulose and hydroxypropyl-cellulose, or time delay materials, including but not limited to, for example, ethyl cellulose and cellulose acetate buryrate can be used.

Hard gelatin capsules can be prepared by, for example, mixing at least one compound according to Formula (I) with at least one inert solid diluent, including but not limited to, for example, calcium carbonate; calcium phosphate; and kaolin. Soft gelatin capsules can be prepared by mixing at least one compound according to Formula (I) with at least one water soluble carrier, including but not limited to, for example, polyethylene glycol; and oil mediums, such as, for example, peanut oil, liquid paraffin, and olive oil.

An aqueous suspension can be prepared by admixing at least one compound according to formula (I) with at least one excipient suitable for the manufacture of an aqueous suspension, including but not limited to, for example, suspending agents, such as, for example, sodium carboxymethylcellulose, methylcellulose, hydroxypropylmethyl-cellulose, sodium alginate, polyvinyl-pyrrolidone, gum tragacanth, and gum acacia; dispersing or wetting agents, such as, for example, a naturally-occurring phosphatide, such as, for example, lecithin; condensation products of alkylene oxide with fatty acids, such as, for example, polyoxyethylene stearate; condensation products of ethylene oxide with long chain aliphatic alcohols, such as, for example heptadecaethyleneoxycetanol; condensation products of ethylene oxide with partial esters derived from fatty acids and a hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can be prepared, for example, by suspending at least one compound according to Formula (I) in either a vegetable oil, such as, for example, arachis oil; olive oil; sesame oil; and coconut oil, or in mineral oil, such as, for example, liquid paraffin. An oily suspension can also contain a thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain a preservative, including but not limited to, for example, an anti-oxidant, such as, for example, butylated hydroxyanisol, and alpha-tocopherol.

Dispersible powders and granules can be prepared by admixing at least one compound according to Formula (I) with at least one dispersing and/or wetting agent; at least one suspending agent; and/or at least one preservative. Suitable dispersing agents, wetting agents, and suspending agents are as already described above. In addition, dispersible powders and granules can also contain excipients, including but not limited to, for example, sweetening agents; flavoring agents; and coloring agents, and/or preservatives including but not limited to, for example, anti-oxidants, such as, for example, ascorbic acid.

An emulsion of at least one compound according to Formula (I) can be prepared as an oil-in-water emulsion. The oil phase can be provided by but is not limited to, for example, a vegetable oil, such as, for example, olive oil and arachis oil; a mineral oil, such as, for example, liquid paraffin; and mixtures thereof. Suitable emulsifying agents include but are not limited to, for example, naturally-occurring phosphatides, such as, for example, soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. An emulsion can also contain a sweetening agent, a flavoring agent, a preservative, and/or an antioxidant.

Syrups and elixirs can contain a sweetening agent, including but not limited to, for example, glycerol; propylene glycol; sorbitol; and sucrose. Syrups and elixirs can also contain a demulcent, a preservative, a flavoring agent, a coloring agent, and/or an antioxidant.

A pharmaceutical composition comprising at least one compound according to Formula (I) can, for example, also be delivered intravenously, subcutaneously, and/or intramuscularly via any acceptable and suitable injectable form, including but not limited to, for example, sterile aqueous solutions comprising acceptable vehicles and solvents, such as, for example, water, Ringer's solution, and isotonic sodium chloride solution; sterile oil-in-water microemulsions; and aqueous or oleagenous suspensions.

A sterile injectable oil-in-water microemulsion can be prepared by 1) dissolving at least one compound according to Formula (I) in an oily phase, such as, for example, a mixture of soybean oil and lecithin; combining the compound containing oil phase with a water and glycerol mixture; and 3) processing the combination to form a microemulsion.

A compound according to Formula (I) can be introduced into a patient's blood-stream by administering the Formula (I) compound containing injectable solution and/or microemulsion as, for example, a local bolus injection. If maintaining a constant circulating concentration of the Formula (I) compound is desired, a continuous intravenous delivery device, such as, for example, a Deltec CADD-PLUS™ model 5400 intravenous pump, can be utilized.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils including but not limited to, for example, synthetic mono- or diglycerides; and fatty acids including but not limited to, for example, oleic acid.

A pharmaceutical composition comprising at least one compound according to Formula (I) can, for example, further be administered via any acceptable and suitable rectal form, including but not limited to, for example, a suppository. A suppository can be prepared by mixing at least one Formula (I) compound with a suitable non-irritating excipient that is liquid at rectal temperatures but solid at least one temperature below rectal temperature. Exemplary non-irritating excipients include but are not limited to, for example, cocoa butter; glycerinated gelatin; hydrogenated vegetable oils; mixtures of polyethylene glycols of various molecular weights; and fatty acid esters of polyethylene glycol.

A compound in accordance with Formula (I) can further be administered via any acceptable and suitable topical route including but not limited to, for example, creams; ointments; jellies; solutions; suspensions, transdermal patches; intranasal inhalers, etc. For purposes of this application, topical application shall include mouth washes and gargles.

Exemplary compositions for nasal aerosol or inhalation administration include solutions that may contain, for example, benzyl alcohol or other suitable preservatives, absorption promoters to enhance absorption and/or bioavailability, and/or other solubilizing or dispersing agents such as those known in the art.

An "effective amount" of a compound in accordance with Formula (I) can be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day.

The specific dose level and frequency of dosage for any particular subject, however, may be varied and generally depends on a variety of factors, including, but not limited to, for example, the bioavailability of the specific Formula (I) compound(s) in the administered form; metabolic stability and length of action of the specific Formula (I) compound(s); species, age, body weight, general health, sex, and diet of the subject; mode and time of administration; rate of excretion; drug combination; and severity of the particular condition.

If formulated as a fixed dose, a combination product can, for example, utilize a dosage of the compound of Formula (I) within the dosage range described above and the dosage of another anti-cancer agent/treatment within the approved dosage range for such known anti-cancer agent/treatment. If a combination product is inappropriate, the compound of Formula (I) and the other anti-cancer agent/treatment can, for example, be administered simultaneously or sequentially. If administered sequentially, the invention is not limited to any particular sequence of administration. For example, compounds of Formula (I) can be administered either prior to, or after, administration of the known anti-cancer agent or treatment.

The compounds of Formula (I) can also be formulated or co-administered with other therapeutic agents that are selected for their particular usefulness in administering therapies associated with the aforementioned conditions. For example, the compounds of the invention may be formulated with agents to prevent nausea, hypersensitivity, and/or gastric irritation, such as, for example, antiemetics and $H_1$ and $H_2$ antihistaminics.

The above other therapeutic agents, when employed in combination with the compounds of Formula (I), can be used, for example, in those amounts indicated in the Physicians' Desk Reference (PDR) or as otherwise determined by one of ordinary skill in the art.

In general, the compounds of Formula (I) can be prepared in accordance with Scheme I and the general knowledge of one skilled in the art. Tautomers and solvates (e.g., hydrates) of the compounds of Formula (I) are also within the scope of the invention. Methods of solvation are generally known in the art. Accordingly, the compounds of the invention can be in the free or hydrate form, and can be obtained by methods exemplified in Scheme I. The abbreviations utilized in Steps 1-5 of Scheme I are as defined in the Examples set forth hereinbelow.

SCHEME I

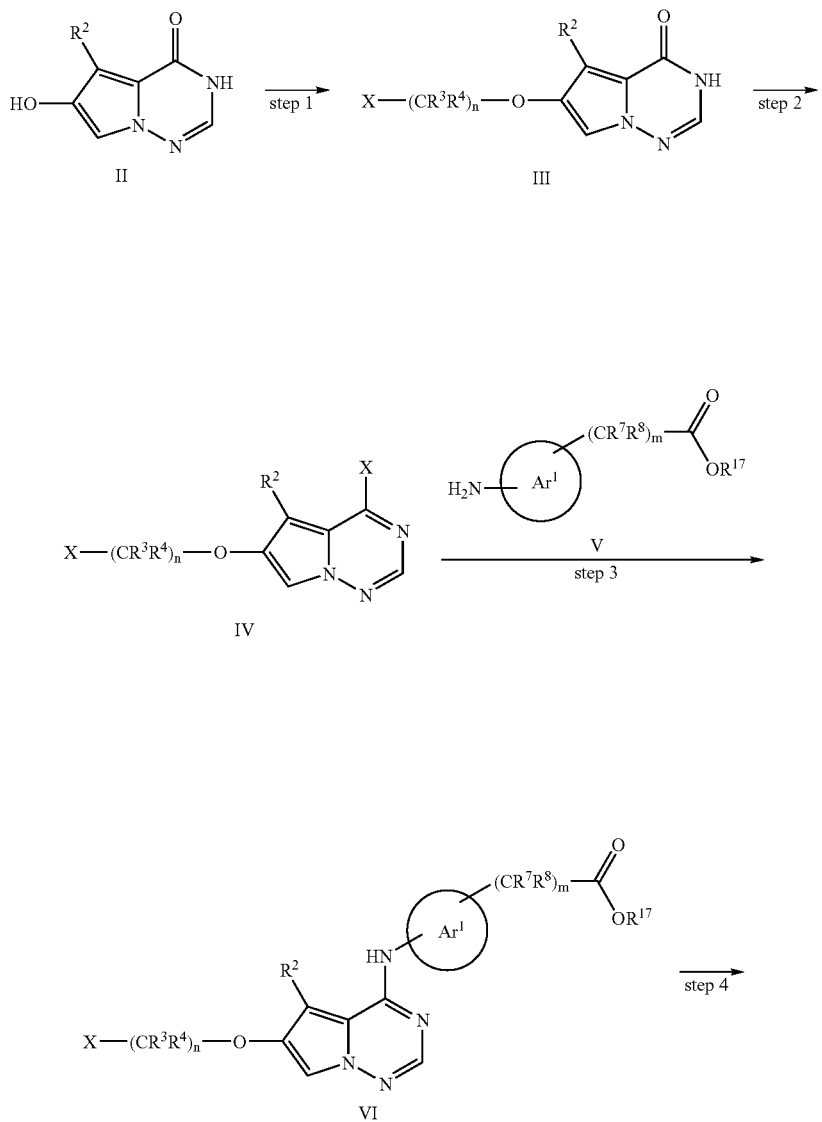

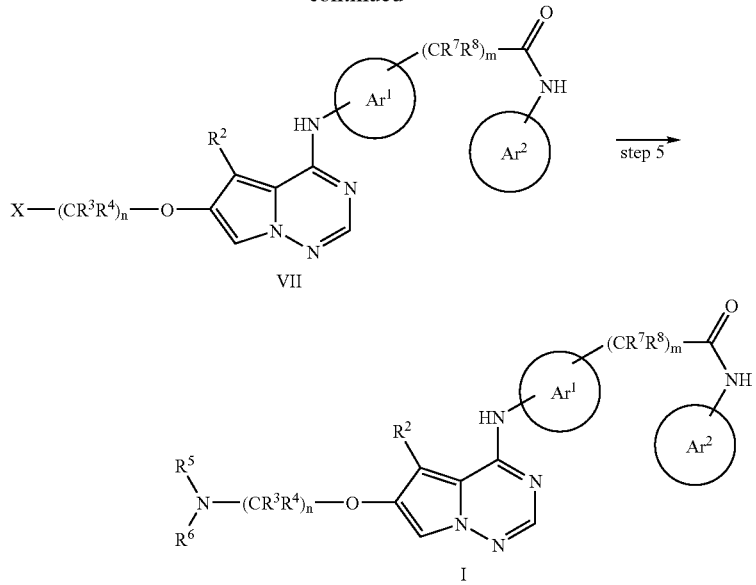

X=halogen and $R^{17}$=lower alkyl

Step 1

Compound III can be obtained by treating compound II with a base, such as, for example, cesium carbonate in an appropriate solvent, such as, for example, acetonitrile, followed by further reaction with a corresponding alkylating agent at elevated temperatures.

Step 2

Compound IV can be obtained by treating compound III with a chlorinating reagent, such as, for example $POCl_3$, in the presence of a base, such as, for example, N,N-diisopropylethylamine.

Step 3

Compound VI can be obtained by coupling compound IV with an appropriately substituted aniline V in the presence of reagents, such as, for example, $Pd_2(DBA)_2$, xanphos, and sodium carbonate in solvent, such as, for example, dioxane.

Step 4

Compound VII can be obtained by hydrolyzing compound VI to the corresponding carboxylic acid under standard conditions, e.g. lithium hydroxide in THF/MeOH/water, followed by subsequent treatment with an appropriate aniline in the presence of a base, such as, for example, diisopropylethylamine.

Step 5

A compound in accordance with Formula (I) is obtained by treating compound VII with an appropriately functionalized primary or secondary amine in the presence of a catalyst, such as, for example, tetrabutylammonium iodide.

It is of import to note that other compounds of Formula (I) can be readily prepared using methods generally known to a person of ordinary skill in the art including but not limited to, for example, the various methods of preparation utilized in the Examples set forth hereinbelow.

ASSAYS

At least one compound of Formula (I), including the compounds described in the examples hereof, has been tested in at least one assay described below and shown activity as an inhibitor of at least one of Aurora kinase A, B, and/or C.

Cell-Based Assay for Histone H3 Phosphorylation

To determine the ability of compounds to inhibit the function of the Aurora kinases in human cells, the phosphorylation status of Histone H3 (HH3) on Serine 10 was analyzed. HH3 is a chromatin protein phosphorylated on at least 2 serine residues including Ser-10 and Ser-28. Ser-10 on centromeric HH3 is phosphorylated in the G2 phase of the cell cycle and by mitosis. Ser-10 is phosphorylated over the entire chromosome. Phosphorylation at this site on HH3 regulates the initiation of chromatin condensation and appears to require the Aurora kinases.

Using this knowledge, an in-cell western assay was developed to measure the extent of HH3 phosphorylation by Aurora kinases in cells arrested in mitosis. Specifically, HCT-116 colorectal cancer cells were plated in a 96 well plate and allowed to grow for 6 hours. After 6 hours, Nocodazole was added to the wells at a final concentration of 15 ug/mL, and the cells were incubated for an additional 16 hours. The Nocodazole treatment caused the cells to arrest in mitosis with maximal HH3 phosphorylation. At the end of the 16 hour Nocodazole treatment, the cells were treated with various concentrations of compounds within the scope of Formula (I) for about 2 hours to determine the ability of such Formula (I) compounds to reverse Aurora Kinase dependent HH3 phosphorylation. At the end of the experiment, Formula (I) compound and control treated cells were fixed in 4% formaldehyde, and then stained with a rabbit polyclonal antibody specific for the epitope containing phosphorylated Ser-10 (Upstate #06-570). At the same time, cells were also stained using a mouse monoclonal to a housekeeping protein (anti-actin, Chemicon 1501R) to control for cell number in each well. Primary antibodies were detected using Alexa dye labeled secondary antibodies (anti-mouse-800 (Rockland #610-131-121), and anti-rabbit-680 (Molecular Probes #A21076)). The assay plates were subsequently analyzed for fluorescence in both channels (800 and 680) using a Licor Odyssey instrument. Fluorescence specific to phospho-HH3 was normalized to fluorescence specific to actin. Percent inhibition of HH3 phosphorylation relative to vehicle treated cells was determined for each concentration of Formula (I) compound tested. The concentration required to give 50% inhibition of HH3 phosphorylation (P-HH3 IC50s) was also determined for each Formula (I) compound tested.

Phenotypic Analysis of Cells Treated with Aurora Kinase Inhibitors

The role of the Aurora kinases in regulating proper cell division has been extensively studied. Genetic disruption of these kinases in model organisms and mammalian cells has demonstrated specific phenotypes associated with loss of Aurora kinase function. Specifically, mitotic defects including the appearance of polyploid cells resulting from failure at cytokinesis is a marked and measurable phenotype in cells lacking Aurora kinase activity. Furthermore, these polyploid cells undergo apoptosis upon subsequent attempts at cell division. Based on these well characterized phenotypes, a functional assay was developed to simultaneously measure polyploidy and apoptosis in cells treated with Aurora kinase inhibitors.

DNA content can be readily quantified by adding propidium iodide (PI) to fixed cells. Propidium iodide binds cellular DNA and fluoresces when illuminated. Fluorescence is directly proportional to cellular DNA content. As a result, one can determine the percentage of cells in a population at each phase of the cell cycle and also the percentage of cells with greater than 4N DNA content (polyploid cells) by using flow cytometry.

Numerous techniques are available to detect apoptosis in mammalian cells. One event that occurs in most cell types once the cell has committed to apoptotic cell death is the specific proteolytic cleavage of the nuclear protein Poly-ADP Ribose Polymerase (PARP). This cleavage is carried out by the apoptosis effector caspases, CASP-3 and CASP-7. Commercial antibodies are available that detect the 85 kDa fragment of cleaved PARP (PARP-p85) present in apoptotic cells but not full length PARP present in living cells. These antibodies are useful for determining the fraction of apoptotic cells in a population at a given time.

By combining PI staining for DNA content and staining for PARP-p85, an assay was developed to track the induction of both polyploidy and apoptosis in cells treated with various concentrations of various Formula (I) compounds. The treated cells were analyzed in accordance with such assay at a variety of times following treatment. By using this assay, the Formula (I) compounds that induced polyploidy after 24 hours of treatment and apoptosis at 48 hours after treatment could be identified, and was consistent with specific inhibition of the Aurora kinases.

Cell Cytotoxicity Assays

To determine the long term effects on cells treated with compounds according to Formula (I), a cytotoxicity assay was used to measure overall cellular viability following 72 hours of Formula (I) compound exposure. The cytotoxicity assay uses soluble tetrazolium salt, MTS, (Promega Corporation; Madison, Wis.) which is metabolically converted to a colored product in living cells but not dead cells.

Cells were seeded in 96 well culture plates. After 24 hours, the Formula (I) compound was added and serial diluted. After 72 hours of exposure, the percent inhibition of MTS conversion relative to vehicle treated cells was determined for each concentration of Formula (I) compound tested. The concentration required to give 50% inhibition of MTS conversion (MTS IC50s) was also determined for each Formula (I) compound tested.

The cytotoxicity assay was performed on at least 12 human cancer cell lines including breast (BT-549, DU4475, MDA-MB-468, MDA-MB-231), prostate (PC-3, DU145, LNCaP), lung (NCI-H446, SHP-77), ovary (A2780), colon (HCT116), and hematologic (CCRF-CEM). This panel of cell lines enabled relative sensitivities of the various lines to cell killing by each Formula (I) compound tested to be determined.

$IC_{50}$ Values

At least one compound of Formula (I) showed activity in at least one of the above referenced assays via an $IC_{50}$ value of between about 0.01 to about 100 µM. In one embodiment, at least one compound of Formula (I) showed activity in at least one of the above referenced assays via an $IC_{50}$ value of less than about 1.0 µM. In another embodiment, at least one compound of Formula (I) showed activity in at least one of the above referenced assays via an $IC_{50}$ value of less than about 0.5 µM.

EXAMPLES

The invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the invention is not limited by the illustrative examples set forth hereinbelow, but rather defined by the claims appended hereto.

All temperatures are in degrees Celsius (° C.) unless indicated otherwise herein.

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

The following abbreviations are employed herein: HOAc: acetic acid, HCl: hydrochloric acid, TFA: trifluoroacetic acid, $CH_3CN$: acetonitrile, MeOH: methanol, EtOAc: ethyl acetate, DMF: dimethyl formamide, THF: tetrahydrofuran, $MgSO_4$: magnesium sulfate, $NaHCO_3$: sodium bicarbonate, HBr: hydrogen bromide, $Pd_2(dba)_3$: Tris(dibenzylideneacetone)dipalladium (0), HATU: O-(7-Azabenzotriazol-1-yl-N,N,N',N'-tetramethyluronim hexafluorophosphate, DMA:

dimethylamine, MeI: methyl iodide, $Cs_2CO_3$: cesium carbonate, $POCl_3$: phosphorous oxychloride, $K_2HPO_4$: dipotassium hydrogen phosphate, MeMgBr: methyl magnesium bromide, EtOH: ethanol, $NH_4Cl$: ammonium chloride, $MeSO_3H$: methylsulfonic acid, $NaHSO_3$: sodium bisulfite, $Na_2CO_3$: bisodium carbonate, NaOH: sodium hydroxide, NaH: sodium hydride, EDC: 1,2-dichloroethane, $NH_2OH$: hydroxylamine, $H_2SO_4$: sulfuric acid, $Pd(OH)_2$: palladium hydroxide, $H_2O_2$: hydrogen peroxide, $N_2$: nitrogen, Bn: benzyl, Me: methyl, Et: ethyl, $H_3PO_4$: phosphoric acid, $LiOH.H_2O$: lithium hydroxide monohydrate, min.: minute(s), h or hr(s): hour(s), L: liter, mL: milliliter, μL: microliter, g: gram(s), mg: milligram(s), mol.: moles, mmol: millimole(s), meq.: milliequivalent, RT or rt: room temperature, ret. t.: HPLC retention time (minutes), sat or sat'd: saturated, aq.: aqueous, TLC: thin layer chromatography, HPLC: high performance liquid chromatography, RP HPLC: analytical reverse phase HPLC, Prep HPLC: preparative reverse phase HPLC, LC/MS: high performance liquid chromatography/mass spectrometry, MS: mass spectrometry, NMR: nuclear magnetic resonance, and mp: melting point.

rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

Example 1

2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-(3-methylphenyl)acetamide

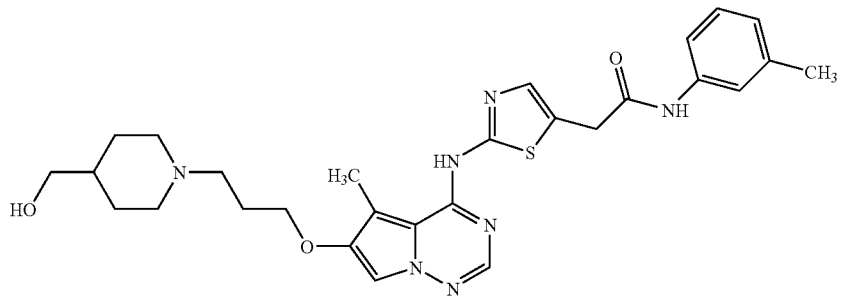

HPLC Conditions:

In Examples 1-20, Analytical Reverse Phase HPLC ret. t. was obtained with a Chromolith SpeedROD column 4.6×50 mm, 4 mL/min flow rate, 4 min. linear gradient elution (unless indicated otherwise herein, all gradients started with 100% solvent A (10% MeOH, 90% $H_2O$, 0.1% TFA) and 0% solvent B, and ended with 100% solvent B (90% MeOH, 10% $H_2O$, 0.1% TFA) and 0% solvent A). UV detection was conducted at 220 nm.

In Examples 21-22, Analytical Reverse Phase HPLC ret. t. was obtained with a Chromolith SpeedROD column 4.6×50 mm, 4 mL/min flow rate, 4 min. linear gradient elution (unless indicated otherwise herein, all gradients started with 100% solvent A (10% MeOH, 90% $H_2O$, 0.2% $H_3PO_4$) and 0% solvent B, and ended with 100% solvent B (90% MeOH, 10% $H_2O$, 0.2% $H_3PO_4$) and 0% solvent A). UV detection was conducted at 254 nm.

Preparative Reverse Phase (RP) HPLC was performed with a linear gradient elution using $H_2O$/MeOH mixtures buffered with 0.1% TFA and detection at 220 nm on one of the following columns: Shimadzu S5 ODS-VP 20×100 mm (flow rate=9 mL/min), or YMC S10 ODS 50×500 mm (flow 1A. 6-(3-chloropropoxy)-5-methylpyrrolo[1,2-f][1,2,4]triazin-4(3H)-one

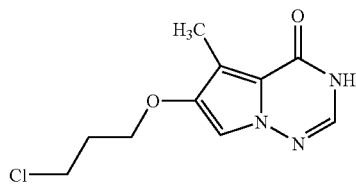

A mixture of 6-hydroxy-5-methylpyrrolo[1,2-f][1,2,4]triazin-4(3H)-one (1.5 g, 9.08 mmol, which was prepared in accordance with the process set forth in provisional patent application Ser. No. 60/583,459), $Cs_2CO_3$ (3.0 g, 9.08 mmol), and 1-bromo-3-chloropropane (894 μL, 9.08 mmol) in $H_2O$/$CH_3CN$/MeOH (10 mL:5 mL:2 mL) was heated to 50° C. for 18 hrs. To the reaction was added 1-bromo-3-chloropropane (300 μL, 3.05 mmol) and heating continued at 50° C. for 4 hrs. The reaction mixture was allowed to cool to rt. and 10 mL of water was added. The solid precipitate was collected by filtration, rinsed with 10 mL H₂O/MeOH and dried under vacuo to give 1.45 g (66%) 1A. RP HPLC ret. t.: 2.38 min. and (M+H)⁺: 242.

1B. 4-chloro-6-(3-chloropropoxy)-5-methylpyrrolo[1,2-f][1,2,4]triazine

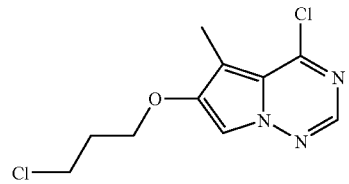

POCl₃ (2 mL, 23 mmol) and diisopropylethylamine (1 mL, 5.79 mmol) were added to a solution of compound 1A in toluene (15 mL) and the reaction mixture was heated to 110° C. for 4 hrs. The reaction mixture was allowed to cool to rt. and concentrated in vacuo. The residue was dissolved in dichloromethane and washed successively with cold 0.5 N HCl, cold aq. NaHCO₃ and brine. The organic layer was dried over MgSO₄, filtered and concentrated to give 1.4 g (93% yield) 1B. RP HPLC ret. t.: 3.26 min.

1C. Methyl 2-(2-(6-(3-chloropropoxy)-5-methylpyrrolo[1,2-f][1,2,4]triazin-4-ylamino)thiazol-5-yl)acetate

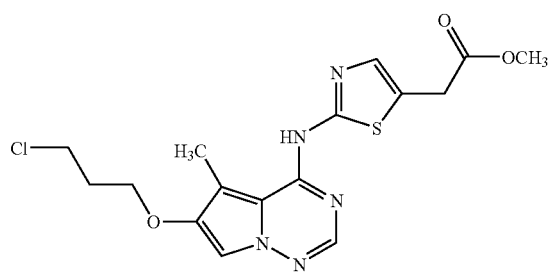

To a mixture of compound 1B (2.8 g, 10.76 mmol) and HBr salt of methyl 2-(2-aminothiazol-5-yl)acetate (3.12 g, 12.33 mmol) in dioxane (60 mL) were added successively sodium carbonate (2.74 g, 25.82 mmol), Pd₂(dba)₃ (197 mg, 0.215 mmol), xantophos (124 mg, 0.215 mmol), and 0.5 mL H₂O. The reaction mixture was degassed and heated at 100° C. under N₂ for 16 h. The mixture was allowed to cool to rt., quenched with water, and extracted with EtOAc. The organic layer was dried and concentrated to give 1C as a brown solid, which was directly used to prepare 1D. RP HPLC ret. t.: 3.27 min. (M+H)⁺: 396.

1D. 2-(2-(6-(3-chloropropoxy)-5-methylpyrrolo[1,2-f][1,2,4]triazin-4-ylamino)thiazol-5-yl)acetic acid

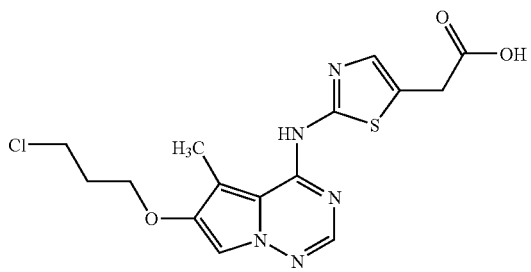

A solution-suspension of compound 1C in THF/MeOH/H₂O (40 mL/20 mL/10 mL) and LiOH.H₂O (1.36 g, 32.28 mmol) was stirred at 60° C. for 30 min., allowed to cool to rt., and concentrated under reduced pressure. Water was added and the resulting mixture was extracted with EtOAc. The aq. layer was separated and acidified with 2 N HCl to produce 2.69 g 1D (65% for 2 steps) as a yellow solid, which was subsequently collected by filtration and dried under vacuum. RP HPLC ret. t.: 2.97 min. and (M+H)⁺: 382.

1E. 2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-(3-methylphenyl)acetamide

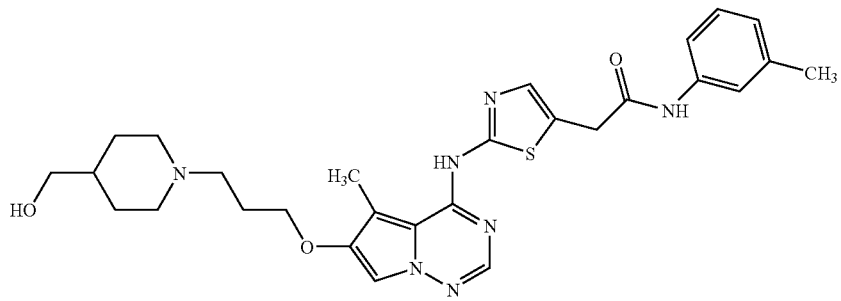

To a solution of 1D (85 mg, 0.223 mmol), 3-methyl aniline (25 mg, 0.234 mmol), and diisopropylethylamine (116 μL, 0.669 mmol) in DMA (0.7 mL) was added HATU (102 mg, 0.268 mmol). After 1 h of stirring at rt., piperidin-4-ylmethanol (250 mg, 2.17 mmol) and tetrabutylammonium iodide (20 mg, 0.05 mmol) were added. The reaction mixture was heated to 90° C. for 3 hrs. and allowed to cool to rt. The reaction was purified by prep HPLC to give 48.6 mg TFA salt of 1E (33%) as a yellow solid. RP HPLC ret. t.: 2.57 min. and (M+H)+: 550.

Examples 2 to 7

Examples 2 to 7, which are set forth in Table 1 hereinbelow, were prepared in accordance with the procedure utilized in preparing Example 1.

TABLE 1

| Example | Compound | HPLC ret. t. (min) | (M + H)+ |
|---|---|---|---|
| 2 | N-(3-chlorophenyl)-2-(2-{[6-({3-[4-(hydroxymethyl)piperidin-1-yl]propyl}oxy)-5-methylpyrrolo[2,1-*f*][1,2,4]triazin-4-yl]amino}-1,3-thiazol-5-yl)acetamide | 2.76 | 570 |
| 3 | N-(3-chloro-4-fluorophenyl)-2-(2-{[6-({3-[4-(hydroxymethyl)piperidin-1-yl]propyl}oxy)-5-methylpyrrolo[2,1-*f*][1,2,4]triazin-4-yl]amino}-1,3-thiazol-5-yl)acetamide | 2.81 | 588 |
| 4 | N-(4-chlorophenyl)-2-(2-{[6-({3-[4-(hydroxymethyl)piperidin-1-yl]propyl}oxy)-5-methylpyrrolo[2,1-*f*][1,2,4]triazin-4-yl]amino}-1,3-thiazol-5-yl)acetamide | 2.72 | 570 |

TABLE 1-continued

| Example | Compound | HPLC ret. t. (min) | (M + H)+ |
|---|---|---|---|
| 5 | 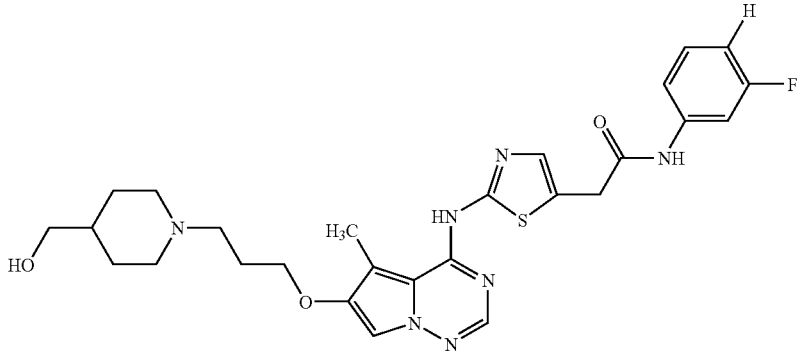<br>N-(3-fluorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide | 2.55 | 554 |
| 6 | 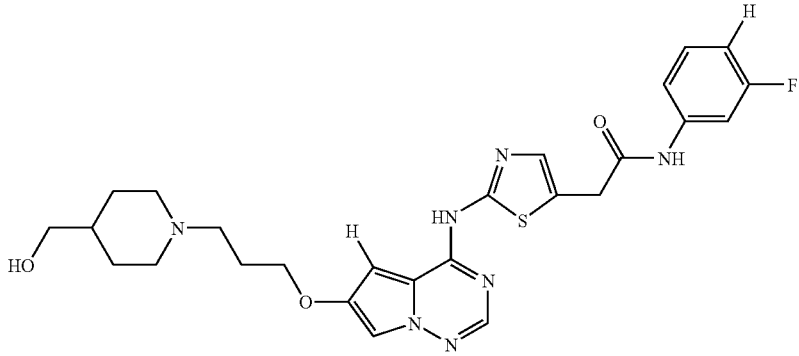<br>N-(3-fluorophenyl)-2-(2-{[6-({3-[4-(hydroxymethyl)piperidin-1-yl]propyl}oxy)pyrrolo[2,1-f][1,2,4]triazin-4-yl]amino}-1,3-thiazol-5-yl)acetamide | 2.47 | 540 |
| 7 | 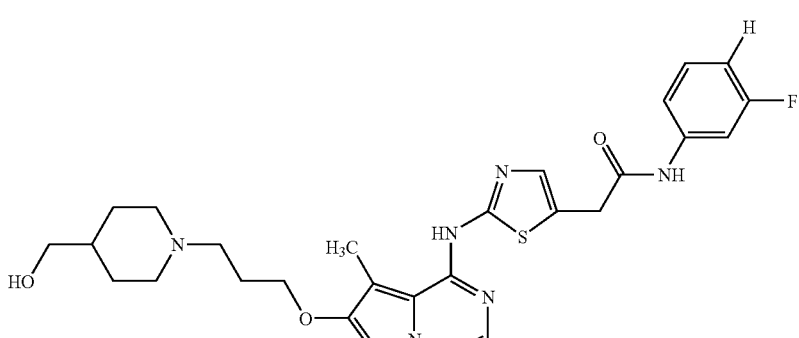<br>2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-phenylacetamide | 2.36 | 536 |

Examples 8 to 16

Examples 8 to 16, which are set forth in Table 2 hereinbelow, were prepared in accordance with the procedure utilized in preparing Example 1.

TABLE 2

| Example | Compound | HPLC ret. t. (min) | (M + H)+ |
|---|---|---|---|
| 8 | 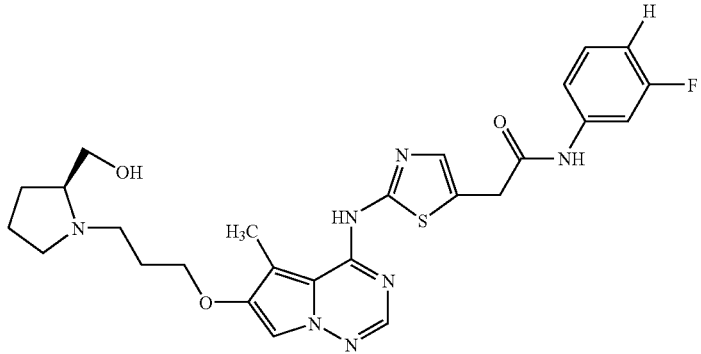<br>N-(3-fluorophenyl)-2-(2-{[6-({3-[(2S)-2-(hydroxymethyl)pyrrolidin-1-yl]propyl}oxy)-5-methylpyrrolo[2,1-f][1,2,4]triazin-4-yl]amino}-1,3-thiazol-5-yl)acetamide | 2.56 | 540 |
| 9 | 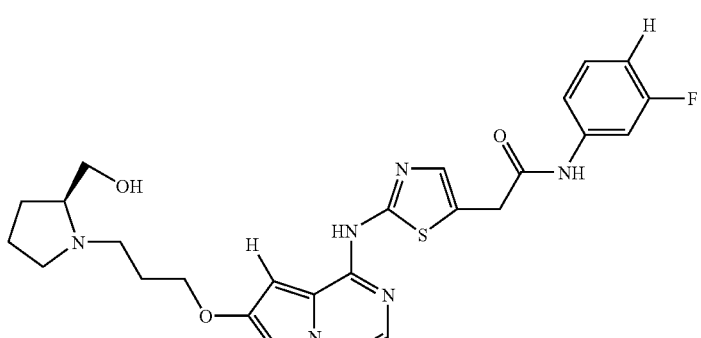<br>N-(3-fluorophenyl)-2-(2-{[6-({3-[(2S)-2-(hydroxymethyl)pyrrolidin-1-yl]propyl}oxy)pyrrolo[2,1-f][1,2,4]triazin-4-yl]amino}-1,3-thiazol-5-yl)acetamide | 2.48 | 526 |
| 10 | 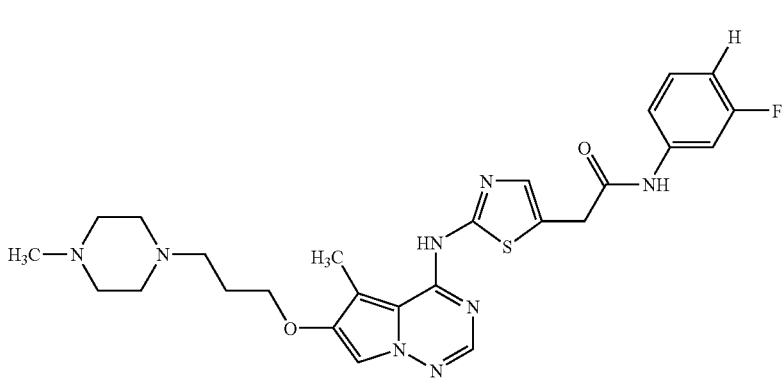<br>N-(3-fluorophenyl)-2-(2-((5-methyl-6-(3-(4-methyl-1-piperazinyl)propoxy)pyrrolo[2,1-f][1,2,4]triazin-4-yl)amino)-1,3-thiazol-5-yl)acetamide | 2.45 | 539 |

TABLE 2-continued

| Example | Compound | HPLC ret. t. (min) | (M + H)+ |
|---|---|---|---|
| 11 | 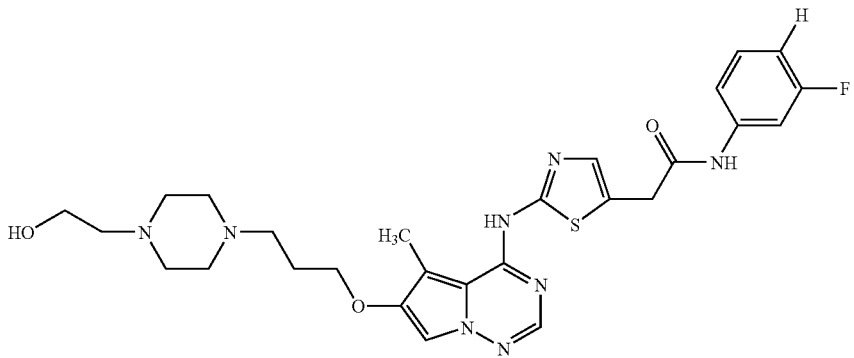<br>N-(3-fluorophenyl)-2-(2-((6-(3-(4-(2-hydroxyethyl)-1-piperazinyl)propoxy)-5-methylpyrrolo[2,1-f][1,2,4]triazin-4-yl)amino)-1,3-thiazol-5-yl)acetamide | 2.38 | 569 |
| 12 | 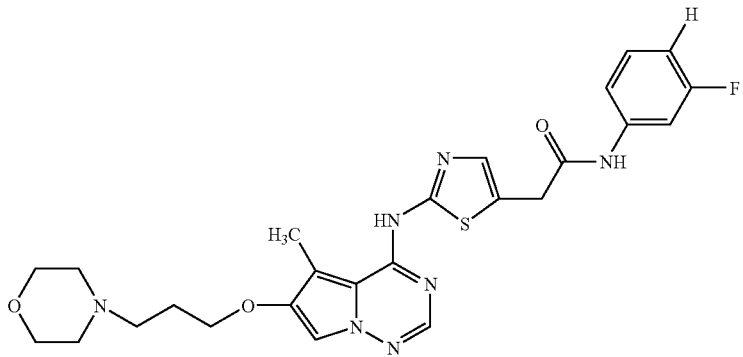<br>N-(3-fluorophenyl)-2-[2-({5-methyl-6-[(3-morpholin-4-ylpropyl)oxy]pyrrolo[2,1-f][1,2,4]triazin-4-yl}amino)-1,3-thiazol-5-yl]acetamide | 2.5 | 526 |
| 13 | 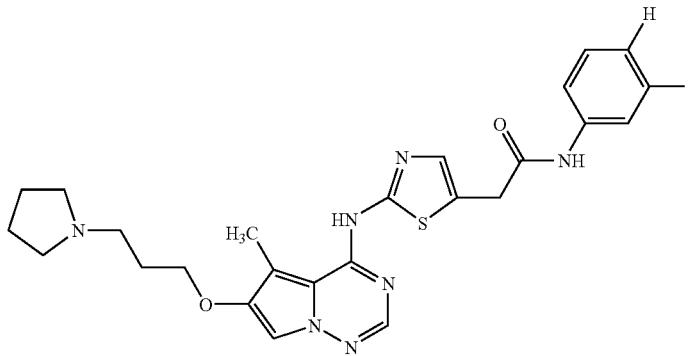<br>N-(3-fluorophenyl)-2-[2-({5-methyl-6-[(3-pyrrolidin-1-ylpropyl)oxy]pyrrolo[2,1-f][1,2,4]triazin-4-yl}amino)-1,3-thiazol-5-yl]acetamide | 2.59 | 510 |

TABLE 2-continued

| Example | Compound | HPLC ret. t. (min) | (M + H)+ |
|---|---|---|---|
| 14 | 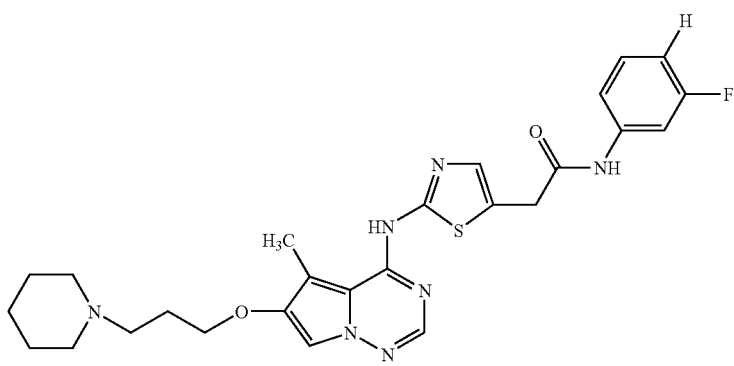<br>N-(3-fluorophenyl)-2-[2-({5-methyl-6-[(3-piperidin-1-ylpropyl)oxy]pyrrolo[2,1-*f*][1,2,4]triazin-4-yl}amino)-1,3-thiazol-5-yl]acetamide | 2.66 | 524 |
| 15 | 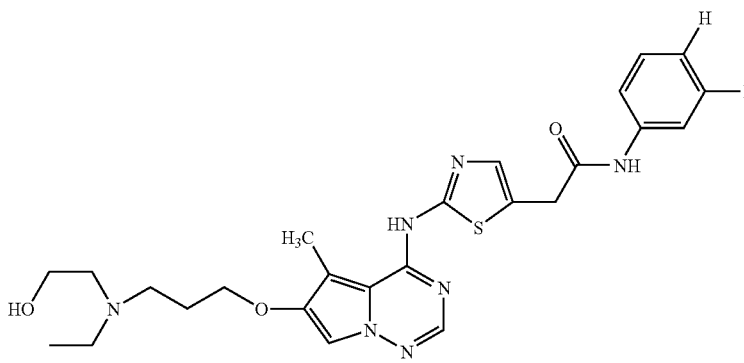<br>2-(2-{[6-({3-[ethyl(2-hydroxyethyl)amino]propyl}oxy)-5-methylpyrrolo[2,1-*f*][1,2,4]triazin-4-yl]amino}-1,3-thiazol-5-yl)-N-(3-fluorophenyl)acetamide | 2.55 | 528 |
| 16 | 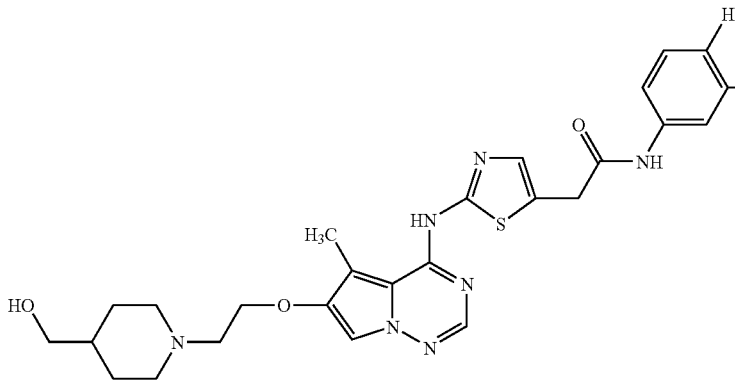<br>N-(3-fluorophenyl)-2-(2-{[6-({2-[4-(hydroxymethyl)piperidin-1-yl]ethyl}oxy)-5-methylpyrrolo[2,1-*f*][1,2,4]triazin-4-yl]amino}-1,3-thiazol-5-yl)acetamide | 2.42 | 540 |

Example 17

N-(3-fluorophenyl)-2-(2-{[6-({3-[4-(hydroxymethyl)piperidin-1-yl]propyl}oxy)-5-(methyloxy)pyrrolo[2,1-j][1,2,4]triazin-4-yl]amino}-1,3-thiazol-5-yl)acetamide

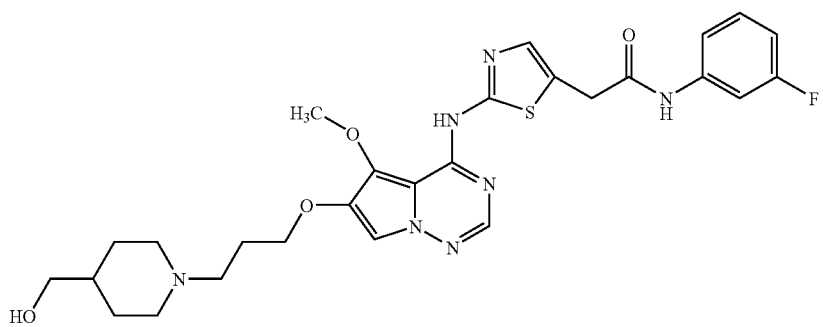

17A. 6-(2-hydroxypropan-2-yl)-5-methoxypyrrolo[1,2-f][1,2,4]triazin-4(3H)-one

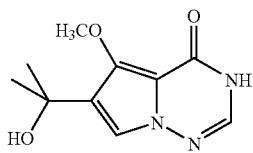

To a stirred mixture of ethyl 5-methoxy-4-oxo-3,4-dihydropyrrolo[1,2-f][1,2,4]triazine-6-carboxylate

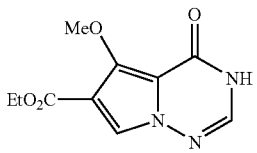

(323 mg, 1.36 mmol) (which can be made in accordance with scheme 2 (wherein R³ is OCH₃, of United States Patent Publication No. 2004/0082582 published Apr. 29, 2004) in 8 mL of THF under N₂ at 0° C. was added dropwise 3M MeMgBr/ether (4.50 mL, 13.5 mmol.) over 10 min. This mixture was stirred at rt. for 2 h, cooled to 0° C. and quenched by dropwise addition of saturated NH₄Cl (5.0 mL). The reaction mixture was partitioned between saturated NH₄Cl (30 mL) and EtOAc (3×40 mL). The combined EtOAc extracts were washed with brine (15 mL), dried (MgSO₄), filtered and concentrated to give 284 mg (93% yield) 17A. RP HPLC ret. t.: 1.36 min. and LC/MS (M+Na)⁺: 246.

17B. 6-hydroxy-5-methoxypyrrolo[1,2-f][1,2,4]triazin-4(3H)-one

To a stirred solution-suspension of 17A (1.23 g, 5.51 mmol) in 16 mL of THF at −5° C. was added dropwise 50% aq. H₂O₂ (2.83 mL) while maintaining the internal temperature between −5° C. and 2° C. This was followed by adding a solution of MeSO₃H (0.85 mL) in water (0.38 mL) while again maintaining the internal temperature between −5° C. and 3° C. The reaction mixture was stirred at 0° C. for 2 h, cooled to −5° C., and quenched by the dropwise addition of a solution of NaHSO₃ (5.39 g) in conc. NH₄OH (7.77 mL) and water (1.71 mL) while maintaining the internal temperature below 25° C. The mixture was stirred at rt. for 20 min and diluted with 27 mL H₂O. The mixture was extracted with THF (2×100 mL). The THF extracts were concentrated in vacuo. The crude solid obtained was mixed with 15 mL H₂O and cooled at 0° C. for 30 min. The precipitated product was collected by filtration to give 0.48 g of 17B. The filtrate was subsequently concentrated in vacuo and purified by an ISCO CombiFlash Companion (Teledyne ISCO, Inc., Lincoln, Nebr.) to provide another 0.30 g 17B (total yield: 0.78 g, 78%). Analytical HPLC ret. t.: 0.64 min. and LC/MS (M+Na)⁺: 204.

17C. 6-(3-chloropropoxy)-5-methoxypyrrolo[1,2-f][1,2,4]triazin-4(3H)-one

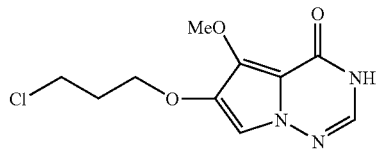

To a stirred solution-suspension of 17B (0.48 g, 2.65 mmol) and Cs₂CO₃ (0.86 g, 2.65 mmol) in 8 mL of MeOH/H₂O (1:1) was added 1-bromo-3-chloropropane (0.42 g, 2.65 mmol). The reaction mixture was heated at 50° C. for 16 h and allowed to cool to rt. The precipitate was filtered to give 0.34 g (50% yield) 17C. RP HPLC ret. t.: 2.12 min. and LC/MS (M+H)⁺: 258.

17D. 4-chloro-6-(3-chloropropoxy)-5-methoxypyrrolo[1,2-f][1,2,4]triazine

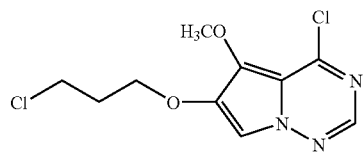

To a stirred mixture of 17C (36.8 mg, 0.14 mmol) and diisopropylethylamine (27.0 μL, 0.16 mmol) in 1 mL of toluene was added POCl₃ (16.0 μL, 0.17 mmol). The reaction mixture was heated at 110° C. for 70 min and more diisopropylethylamine (27.0 μL, 0.16 mmol) and POCl₃ (16.0 μL, 0.17 mmol) were added. The reaction mixture was heated at 110° C. for another 80 min., allowed to cool to rt., concentrated in vacuo, and subsequently partitioned between 20 mL sat. K₂HPO₄ solution and EtOAc (2×40 mL). The combined EtOAc extracts were washed with brine (15 mL), dried (MgSO₄), filtered, and concentrated in vacuo to give 17D in a quantitative yield. This compound was used in the next step without any further purification. RP HPLC ret. t.: 2.94 min. and LC/MS (M+H)⁺: 276.

17E. N-(3-fluorophenyl)-2-(2-{[6-({3-[4-(hydroxymethyl)piperidin-1-yl]propyl}oxy)-5-(methyloxy)pyrrolo[2,1-f][1,2,4]triazin-4-yl]amino}-1,3-thiazol-5-yl)acetamide

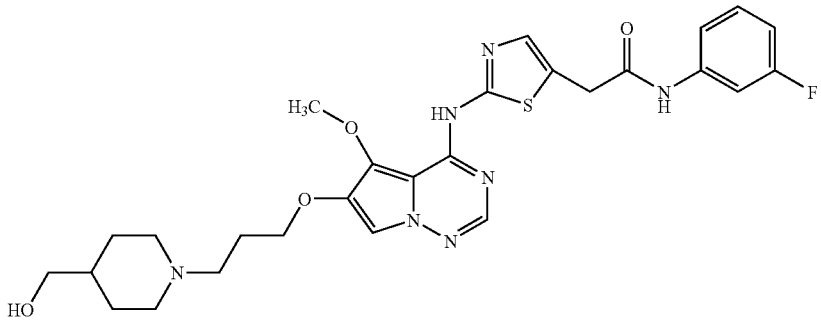

To a stirred mixture of 17D (43.0 mg, 0.16 mmol), Na₂CO₃ (39.6 mg, 0.38 mmol), Pd₂(dba)₃ (4.2 mg) and Xantphos (2.6 mg) in 1.5 mL of anhydrous dioxane under N₂ was added the TFA salt of 2-(2-aminothiazol-5-yl)-N-(3-fluorophenyl)acetamide (58.0 mg, 0.16 mmol). The reaction mixture was heated at 100° C. for 17 h, allowed to cool to rt., and concentrated. The resulting crude was dissolved in 1 mL of DMA and combined with 4-hydroxymethylpiperidine (89.0 mg, 0.77 mmol). The mixture was heated at 90° C. for 5 h, allowed to cool to rt., and purified by prep. HPLC to give 14 mg 17E (17% yield). RP HPLC ret. t.: 2.53 min. and LC/MS (M+H)⁺: 570.

Example 18
N-(3-fluorophenyl)-2-(2-{[6-({3-[(2S)-2-(hydroxymethyl)pyrrolidin-1-yl]propyl}oxy)-5-(methyloxy)pyrrolo[2,1-f][1,2,4]triazin-4-yl]amino}-1,3-thiazol-5-yl)acetamide

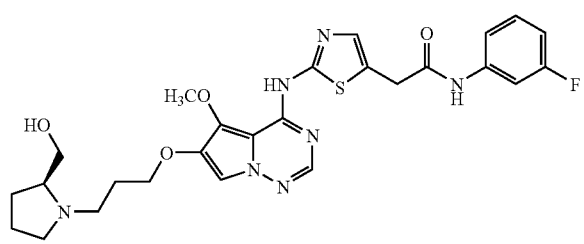

Example 18 was prepared in accordance with the procedure used to prepare Example 17, wherein compound 17N (50.0 mg, 0.18 mmol), 2-(2-aminothiazol-5-yl)-N-(3-fluorophenyl)acetamide TFA salt (60.0 mg, 0.18 mmol), and L-prolinol (183.2 mg, 1.80 mmol) were utilized to produce 16 mg Example 18 (15% yield). RP HPLC ret. t.: 2.60 min. and LC/MS (M+H)⁺: 556.

Example 19

2-(2-{[6-({3-[(2S)-2-(hydroxymethyl)pyrrolidin-1-yl]propyl}oxy)-5-methylpyrrolo[2,1-][1,2,4]triazin-4-yl]amino}-1,3-thiazol-5-yl)-N-phenylacetamide

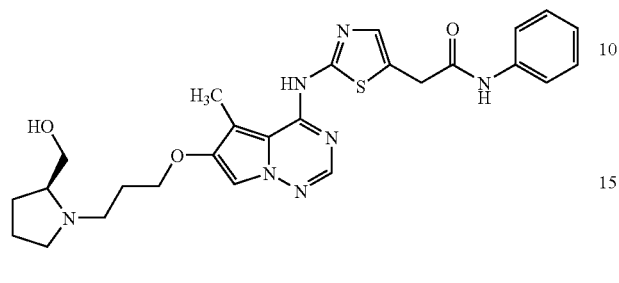

Example 19 was prepared in accordance with the procedure used to prepare Example 1. RP HPLC ret. t.: 2.36 min. and LC/MS (M+H)+: 522.

Example 20

N-(2-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide

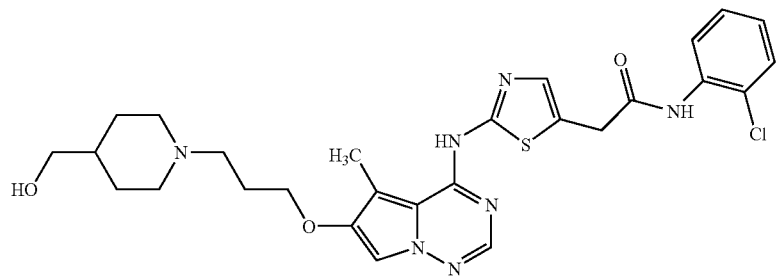

Example 20 was prepared in accordance with the procedure utilized to prepare Example 1. RP HPLC ret. t.: 2.46 min. and LC/MS (M+H)+: 570.

Example 21

N-(3-fluorophenyl)-2-(5-{[6-({3-[4-(hydroxymethyl)piperidin-1-yl]propyl}oxy)-5-methylpyrrolo[2,1-f][1,2,4]triazin-4-yl]amino}-1H-pyrazol-3-yl)acetamide

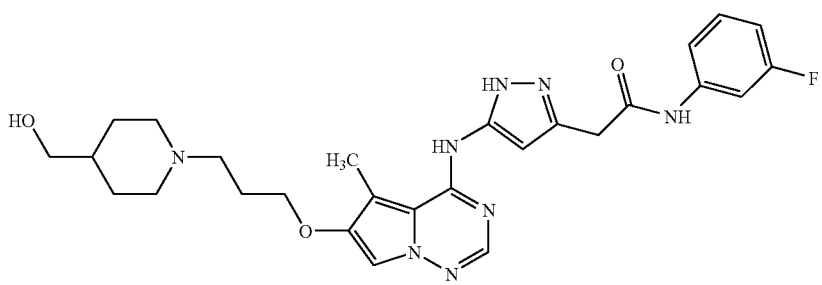

21A. Methyl 2-(5-(6-(3-chloropropoxy)-5-methylpyrrolo[1,2-f][1,2,4]triazin-4-ylamino)-1H-pyrazol-3-yl)acetate

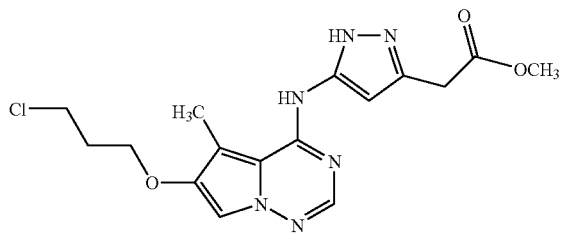

21A was prepared by combining 1B and methyl 2-(5-amino-1H-pyrazol-3-yl)acetate in accordance with procedure used to prepare Example 1. RP HPLC ret. t.: 2.32 min. and LC/MS (M+H)$^+$: 379.

21B. 2-(5-(6-(3-chloropropoxy)-5-methylpyrrolo[1,2-f][1,2,4]triazin-4-ylamino)-1H-pyrazol-3-yl)acetic acid

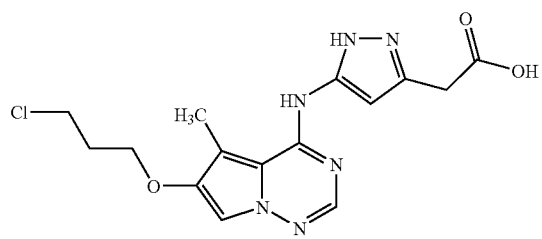

A mixture of 21A (170 mg, 0.45 mmol) and lithium hydroxide monohydrate (40 mg, 0.9 mmol) in THF/H$_2$O (3 mL, 2:1) was stirred for 1 hr. Aq. 1N HCl was added dropwise to pH 3.0, the solvents were removed under reduced pressure and the residue was dried under high vacuum to give 21B as a light orange solid. RP HPLC ret. t.: 2.13 min. and (M+H)$^+$: 365.

21C. 2-(5-(6-(3-chloropropoxy)-5-methylpyrrolo[1,2-f][1,2,4]triazin-4-ylamino)-1H-pyrazol-3-yl)-N-(3-fluorophenyl)acetamide

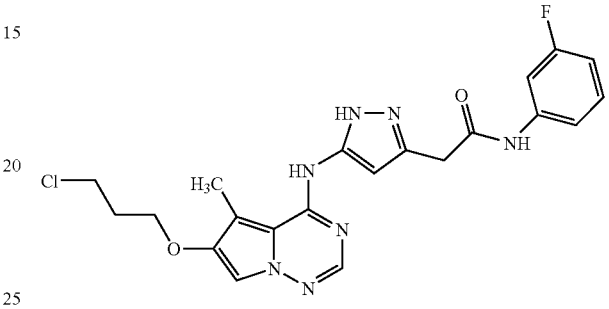

To a mixture of 21B (164 mg, 0.45 mmol), 3-fluoroaniline (0.087 mL, 0.9 mmol), 2-hydroxypyridine N-oxide (75 mg, 0.675 mmol) and triethylamine (0.25 mL, 1.8 mmol) in 4 mL of dry DMF was added EDC (121 mg, 0.63 mmol). The mixture was stirred at rt. for 16 h, cooled to 0° C., and water added dropwise to produce 105 mg (51% yield) 21C as a white solid precipitate, which was subsequently collected by filtration, rinsed with water, and dried under high vacuum. RP HPLC ret. t.: 2.83 min. and (M+H)$^+$: 458.

21D. N-(3-fluorophenyl)-2-(5-{[6-({3-[4-(hydroxymethyl)piperidin-1-yl]propyl}oxy)-5-methylpyrrolo[2,1-f][1,2,4]triazin-4-yl]amino}-1H-pyrazol-3-yl)acetamide

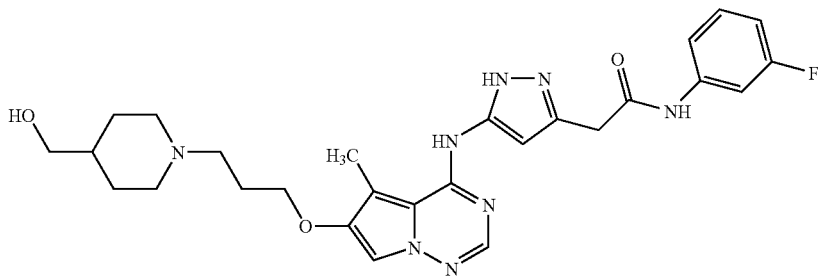

21D was prepared from 21C by utilizing 4-hydroxymethylpiperidine in accordance with the process used to prepare Example 1. RP HPLC ret. t.: 1.92 min. and LC/MS (M+H)$^+$: 537.

Example 22

N-(3-fluorophenyl)-2-(5-{[6-({3-[(2S)-2-(hydroxymethyl)pyrrolidin-1-yl]propyl}oxy)-5-methylpyrrolo[2,1-f][1,2,4]triazin-4-yl]amino}-1H-pyrazol-3-yl)acetamide

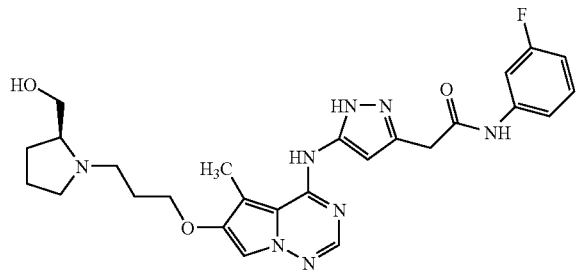

Example 22 was prepared from 21C by utilizing (2S)-2-hydroxymethylpyrrolidine in accordance with the process used to prepare Example 1. RP HPLC ret. t.: 1.92 min. and LC/MS (M+H)$^+$: 523.

What is claimed is:

1. A compound of the formula:

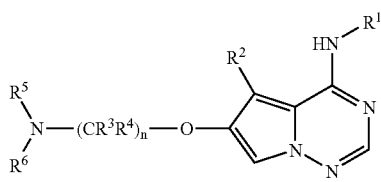

wherein:

R$^1$ is

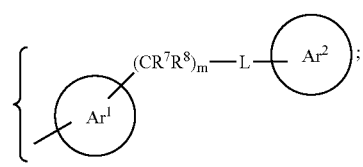

R$^2$ is H, lower alkyl, halogen, or —OR$^9$;
R$^3$ and R$^4$ are independently H, lower alkyl, substituted lower alkyl, OR$^{10}$, or NR$^{11}$R$^{12}$;
n is an integer from 2-6;
R$^5$ and R$^6$ are independently H, alkyl, substituted alkyl, or taken together with the N to which they are attached form a 4 to 7-membered heterocyclic or substituted heterocyclic ring optionally containing at least two heteroatoms;
R$^7$ and R$^8$ are independently H, alkyl, or substituted alkyl;
m is an integer from 1-3;
L is —OC(=O)NH—, —O—, —C(=O)NH—, —NHC(=O)—, or —NHS(=O)$_2$—;
R$^9$ is H or lower alkyl;
R$^{10}$ is H, alkyl, substituted alkyl, alkylamino, or substituted alkylamino;
R$^{11}$ and R$^{12}$ are independently H, alkyl, or substituted alkyl; and Ar$^1$ and Ar$^2$ are independently aryl, substituted aryl, heteroaryl, or substituted heteroaryl,
or a pharmaceutically acceptable salt thereof.

2. A compound according to claim 1, wherein R$^1$ is

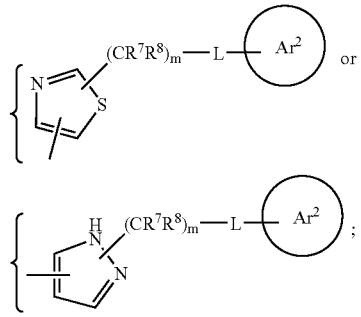

or a pharmaceutically acceptable salt thereof.

3. A compound according to claim 1, wherein R$^5$ and R$^6$ are taken together with the N to which they are attached to form a 4 to 7-membered heterocyclic or substituted heterocyclic ring containing at least two heteroatoms selected from the group consisting of O, S, and N,
or a pharmaceutically acceptable salt thereof.

4. A compound according to claim 1, wherein R$^5$ and R$^6$ are taken together with the nitrogen to which they are attached to form a 5- or 6-membered heterocyclic or substituted heterocyclic ring containing at least two heteroatoms selected from the group consisting of O and N,
or a pharmaceutically acceptable salt thereof.

5. A compound according to claim 4, wherein R$^5$ and R$^6$ are taken together with the N to which they are attached to form morpholinyl,
or a pharmaceutically acceptable salt thereof.

6. A compound according to claim 1, wherein R$^2$ is H or lower alkyl,
or a pharmaceutically acceptable salt thereof.

7. A compound according to claim 6, wherein R$^2$ is methyl, ethyl, or isopropyl,
or a pharmaceutically acceptable salt thereof.

8. A compound according to claim 1, wherein R$^3$, R$^4$, R$^7$ and R$^8$ are independently H or lower alkyl,
or a pharmaceutically acceptable salt thereof.

9. A compound according to claim 8, wherein R$^3$, R$^4$, R$^7$ and R$^8$ are each H,
or a pharmaceutically acceptable salt thereof.

10. A compound according to claim 1, wherein R$^5$ and R$^6$ are taken together with the N to which they are attached to form a 5- or 6-membered heterocyclic or substituted heterocyclic ring,
or a pharmaceutically acceptable salt thereof.

11. A compound according to claim 1, wherein R$^5$ and R$^6$ are taken together with the N to which they are attached to form a 5- or 6-membered substituted heterocyclic ring substituted with at least one alkyl or hydroxyalkyl substituent,
or a pharmaceutically acceptable salt thereof.

12. A compound according to claim 1, wherein L is —C(=O)NH— or —NHC(=O)—,
or a pharmaceutically acceptable salt thereof.

13. A compound according to claim 1, wherein Ar$^2$ is aryl or substituted aryl,
or a pharmaceutically acceptable salt thereof.

14. A compound according to claim 13, wherein Ar$^2$ is a substituted aryl substituted with at least one substituent selected from the group consisting of H, halogen, cyano, lower alkyl, and OR¹³, wherein R¹³ is lower alkyl, or a pharmaceutically acceptable salt thereof.

15. A compound according to claim 1, wherein n is 2 or 3, or a pharmaceutically acceptable salt thereof.

16. A compound according to claim 1, wherein Ar² is

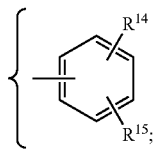

wherein R¹⁴ and R¹⁵ are independently H, halogen, or methyl, or a pharmaceutically acceptable salt thereof.

17. A compound according to claim 1, wherein m is 1, or a pharmaceutically acceptable salt thereof.

18. A compound according to claim 1, having the formula:

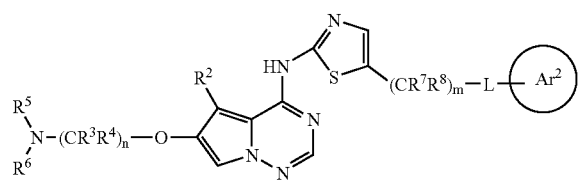

or a pharmaceutically acceptable salt thereof.

19. A compound according to claim 1, having the formula:

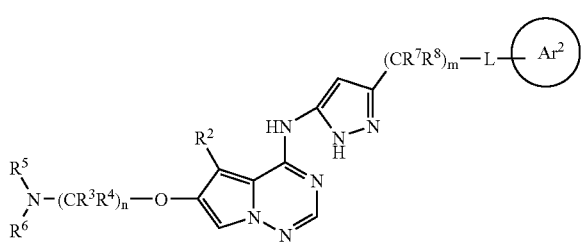

or a pharmaceutically acceptable salt thereof.

20. A compound according to claim 1, which is (i) selected from the group consisting of 2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-(3-methylphenyl)acetamide;

N-(3-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide;

N-(3-chloro-4-fluorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide;

N-(4-chlorophenyl)-2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)acetamide;

N-(3-fluorophenyl)-2-(2-{[6-({3-[4-(hydroxymethyl)piperidin-1-yl]pro-pyl}oxy)-5-methylpyrrolo[2,1-f][1,2,4]triazin-4-yl]amino}-1,3-thiazol-5-yl)acetamide;

N-(3-fluorophenyl)-2-(2-{[6-({3-[4-(hydroxymethyl)piperidin-1-yl]propyl}oxy)pyrrolo[2,1-f][1,2,4]triazin-4-yl]amino}-1,3-thiazol-5-yl)acetamide;

2-(2-{[6-({3-[4-(hydroxymethyl)piperidin-1-yl]propyl}oxy)-5-methylpyrrolo[2,1-f][1,2,4]triazin-4-yl]amino}-1,3-thiazol-5-yl)-N-phenylacetamide;

N-(3-fluorophenyl)-2-(2-{[6-({3-[(2S)-2-(hydroxymethyl)pyrrolidin-1-yl]propyl}oxy)-5-methylpyrrolo[2,1-f][1,2,4]triazin-4-yl]amino}-1,3-thiazol-5-yl)acetamide;

N-(3-fluorophenyl)-2-(2-{[6-({3-[(2S)-2-(hydroxymethyl)pyrrolidin-1-yl]propyl}oxy)pyrrolo[2,1-][1,2,4]triazin-4-yl]amino}-1,3-thiazol-5-yl)acetamide;

N-(3-fluorophenyl)-2-(2-((5-methyl-6-(3-(4-methyl-1-piperaziny)propoxy)pyrrolo[2,1-f][1,2,4]triazin-4-yl)amino)-1,3-thiazol-5-yl)acetamide;

N-(3-fluorophenyl)-2-(2-((6-(3-(4-(2-hydroxyethyl)-1-piperazinyl)propoxy)-5-methylpyrrolo[2,1-f][1,2,4]triazin-4-yl)amino)-1,3-thiazol-5-yl)acetamide;

N-(3-fluorophenyl)-2-[2-({5-methyl-6-[(3-morpholin-4-ylpropyl)oxy]pyrrolo[2,1-f][1,2,4]triazin-4-yl}amino)-1,3-thiazol-5-yl]acetamide;

N-(3-fluorophenyl)-2-[2-({5-methyl-6-[(3-pyrrolidin-1-ylpropyl)oxy]pyrrolo[2,1-f][1,2,4]triazin-4-yl}amino)-1,3-thiazol-5-yl]acetamide;

N-(3-fluorophenyl)-2-[2-({5-methyl-6-[(3-piperidin-1-ylpropyl)oxy]pyrrolo[2,1-f][1,2,4]triazin-4-yl}amino)-1,3-thiazol-5-yl]acetamide;

2-(2-{[6-({3-[ethyl(2-hydroxyethyl)amino]propyl}oxy)-5-methylpyrrolo[2,1-f][1,2,4]triazin-4-yl]amino}-1,3-thiazol-5-yl)-N-(3-fluorophenyl)acetamide;

N-(3-fluorophenyl)-2-(2-{[6-({2-[4-(hydroxymethyl)piperidin-1-yl]ethyl}oxy)-5-methylpyrrolo[2,1-f][1,2,4]triazin-4-yl]amino}-1,3-thiazol-5-yl)acetamide;

N-(3-fluorophenyl)-2-(2-{[6-({3-[4-(hydroxymethyl)piperidin-1-yl]propyl}oxy)-5-(methyloxy)pyrrolo[2,1-f][1,2,4]triazin-4-yl]amino}-1,3-thiazol-5-yl)acetamide;

N-(3-fluorophenyl)-2-(2-{[6-({3-[(2S)-2-(hydroxymethyl)pyrrolidin-1-yl]propyl}oxy)-5-(methyloxy)pyrrolo[2,1-f][1,2,4]triazin-4-yl]amino}-1,3-thiazol-5-yl)acetamide;

2-(2-{[6-({3-[(2S)-2-(hydroxymethyl)pyrrolidin-1-yl]propyl}oxy)-5-methylpyrrolo[2,1-][1,2,4]triazin-4-yl]amino}-1,3-thiazol-5-yl)-N-phenylacetamide;

N-(2-chlorophenyl)-2-(2-{[6-({3-[4-(hydroxymethyl)piperidin-1-yl]propyl}oxy)-5-methylpyrrolo[2,1-][1,2,4]triazin-4-yl]amino}-1,3-thiazol-5-yl)acetamide; and methyl 2-(5-(6-(3-chloropropoxy)-5-methylpyrrolo[1,2-f][1,2,4]triazin-4-ylamino)-1H-pyrazol-3-yl)acetate; or (ii) a pharmaceutically acceptable salt thereof.

21. A pharmaceutical composition comprising
an active agent which is a compound or pharmaceutically acceptable salt according to claim 1 or 20; and
at least one pharmaceutically-acceptable carrier or diluent.

22. A method for treating at least one proliferative disease comprising administering, to a patient in need thereof, a therapeutically effective amount of the pharmaceutical composition according to claim 21, wherein the proliferative disease is breast cancer or rheumatoid arthritis.

23. The pharmaceutical composition according to claim 21, further comprising another active agent, which comprises an anti-cancer agent.

* * * * *

UNITED STATES PATENT AND TRADEMARK OFFICE
CERTIFICATE OF CORRECTION

PATENT NO. : 7,402,582 B2
APPLICATION NO. : 11/475808
DATED : July 22, 2008
INVENTOR(S) : Ashvinikumar V. Gavai et al.

It is certified that error appears in the above-identified patent and that said Letters Patent is hereby corrected as shown below:

ON THE TITLE PAGE [56] REFERENCES CITED:

Foreign Patent Documents, "WO00/71129" should read --WO2000/71129--; and "WO02/40486" should read --WO2002/40486--.

COLUMN 2:

Line 54, "form" should read --to form--.

COLUMN 3:

Line 53, "morpholin-4-ylpropyl)oxy]pyrrolo[2,1-j][1,2,4]triazin-4-" should read --morpholin-4-ylpropyl)oxy]pyrrolo[2,1-f][1,2,4]triazin-4--.

COLUMN 4:

Line 7, "methylpyrrolo[2,1-j][1,2,4]triazin-4-yl]amino}-1,3-thiazol-" should read --methylpyrrolo[2,1-f][1,2,4]triazin-4-yl]amino}-1,3-thiazol- --.

COLUMN 9:

Line 34, "4" should read --4- --;
Line 35, "to 7 membered monocyclic, 7 to 11 membered bicyclic, or 10" should read --to 7-membered monocyclic, 7- to 11- membered bicyclic, or 10- --; and
Line 36, "15 membered" should read --15-membered--.

COLUMN 10:

Line 22, "a" should read --an--; and
Line 30, "an" should read --and--.

COLUMN 11:

Line 1, "form" should read --from--; and
Line 10, "form" should read --from--.

UNITED STATES PATENT AND TRADEMARK OFFICE
CERTIFICATE OF CORRECTION

PATENT NO. : 7,402,582 B2
APPLICATION NO. : 11/475808
DATED : July 22, 2008
INVENTOR(S) : Ashvinikumar V. Gavai et al.

It is certified that error appears in the above-identified patent and that said Letters Patent is hereby corrected as shown below:

COLUMN 35:

Line 1, "vacuo" should read --vacuum--.

COLUMN 55:

Line 55, "4 to 7-membered" should read --4- to 7-membered--.

COLUMN 56:

Line 23, "4 to 7-membered" should read --4- to 7-membered--.

COLUMN 57:

Line 48, "of" should read --of:--.

COLUMN 58:

Line 50, "comprising" should read --comprising:--.

Signed and Sealed this

Tenth Day of March, 2009

JOHN DOLL
*Acting Director of the United States Patent and Trademark Office*